United States Patent
Garciá et al.

(10) Patent No.: US 12,382,829 B2
(45) Date of Patent: Aug. 5, 2025

(54) COMPOUND AND AN ORGANIC SEMICONDUCTING LAYER, AN ORGANIC ELECTRONIC DEVICE AND A DISPLAY OR LIGHTING DEVICE COMPRISING THE SAME

(71) Applicant: Novaled GmbH, Dresden (DE)

(72) Inventors: Elena Galán Garciá, Dresden (DE); Benjamin Schulze, Dresden (DE); Julien Frey, Dresden (DE)

(73) Assignee: Novaled GmbH, Dresden (DE)

( * ) Notice: Subject to any disclaimer, the term of this patent is extended or adjusted under 35 U.S.C. 154(b) by 844 days.

(21) Appl. No.: 17/605,944

(22) PCT Filed: Apr. 20, 2020

(86) PCT No.: PCT/EP2020/060978
§ 371 (c)(1),
(2) Date: Oct. 22, 2021

(87) PCT Pub. No.: WO2020/216708
PCT Pub. Date: Oct. 29, 2020

(65) Prior Publication Data
US 2022/0209135 A1   Jun. 30, 2022

(30) Foreign Application Priority Data
Apr. 24, 2019   (EP) .................................. 19170921

(51) Int. Cl.
| | |
|---|---|
| *C09K 11/06* | (2006.01) |
| *C07D 221/18* | (2006.01) |
| *C07D 401/10* | (2006.01) |
| *H10K 85/60* | (2023.01) |
| *H10K 50/165* | (2023.01) |
| *H10K 101/30* | (2023.01) |

(52) U.S. Cl.
CPC ....... *H10K 85/6572* (2023.02); *C07D 221/18* (2013.01); *C07D 401/10* (2013.01); *C09K 11/06* (2013.01); *H10K 85/615* (2023.02); *H10K 85/654* (2023.02); *C09K 2211/1018* (2013.01); *H10K 50/165* (2023.02); *H10K 2101/30* (2023.02)

(58) Field of Classification Search
CPC ............ H10K 85/6572; H10K 85/654; H10K 85/615; H10K 2101/30; H10K 50/165; C09K 11/06; C09K 2211/1018; C07D 221/18; C07D 401/10
See application file for complete search history.

(56) References Cited

U.S. PATENT DOCUMENTS

| | | | |
|---|---|---|---|
| 3,751,259 A * | 8/1973 | Bauer | C08K 5/3437 430/920 |
| 2016/0005980 A1* | 1/2016 | Ito | C09B 57/10 257/40 |
| 2016/0233434 A1 | 8/2016 | Jeong et al. | |

FOREIGN PATENT DOCUMENTS

| | | |
|---|---|---|
| CN | 104693174 A | 6/2015 |
| EP | 3312899 A1 | 4/2018 |
| EP | 3369729 A1 | 9/2018 |
| KR | 20160004466 A | 1/2016 |
| WO | 2017089399 A1 | 6/2017 |
| WO | 2017102822 A1 | 6/2017 |
| WO | 2018097648 A1 | 5/2018 |
| WO | 2018158438 A1 | 9/2018 |

OTHER PUBLICATIONS

Hervieu et al., 257(16) Compt. Rend. 2300-2 (1963) (Year: 1963).*
Smith et al., 16(3) J. Heterocyclic Chem. 421-5 (1979) (Year: 1979).*
Hansch et al., 86(8) J. Am. Chem. Soc. 1616-26 (1964) (Year: 1964).*
Mock et al., 26(10) Australian J. Chem. 2315-9 (1973) (Year: 1973).*
International Search Report and Written Opinion issued in international application No. PCT/EP2020/060978, mailed Sep. 21, 2020 (24 pages).
Notice to File a Response issued in Korea application No. 10-2021-7037950, dated Jul. 4, 2024 (18 pages).
Database Registry [Online], CAS Registry No. 94300-71-7 (Jan. 21, 1985).
Database Registry [Online], CAS Registry No. 111228-16-1 (Nov. 7, 1987).
Database Registry [Online], CAS Registry No. 412323-11-6 (May 8, 2002).

(Continued)

*Primary Examiner* — Timothy R Rozof
(74) *Attorney, Agent, or Firm* — Eversheds Sutherland (US) LLP

(57) ABSTRACT

The present invention relates to a compound having the formula (I), an organic semiconducting layer comprising the same, an organic electronic device comprising the same, a display device comprising the same and a lighting device comprising the same.

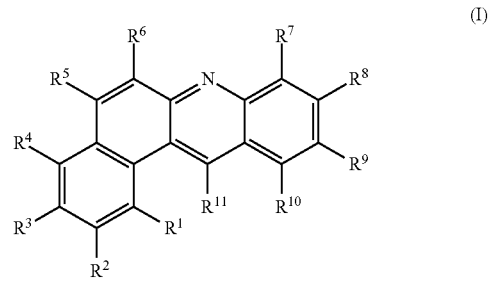

13 Claims, 2 Drawing Sheets

(56) References Cited

OTHER PUBLICATIONS

Hauser et al., A New Method for the Synthesis of Certain Benz[a]acridines 1, Journal of the American Chemical Society, vol. 77, No. 14, Jul. 1, 1955, pp. 3858-3860.
Sawicki et al., Paper and thin-layer electrophoretic separations of polynuclear aza heterocyclic compounds, Journal of Chromatograph, vol. 30, Jan. 1, 1967, pp. 522-527.
Zhang et al., Studies directed towards nonyl acridine orange analogues having the potential to act as FRET donors with the PDT drug Pc 4, RSC Advances, vol. 6, No. 35, Jan. 1, 2016, pp. 29391-29403.
Mock et al., Synthesis of some derivatives of Benz[a]acridine and Benz[c]acridine, Australian Journal of Chemistry: An International Journal for Chemical Science, vol. 26, No. 10, Jan. 1, 1973, p. 2315.
Hansch et al., p -[sigma]-[pi] Analysis. A Method for the Correlation of Biological Activity and Chemical Structure, Journal of the American Chemical Society, vol. 86, No. 8, Apr. 1, 1964, pp. 1616-1626.
Liu et al., Conversion and distribution of nitrogen-containing compounds of Liaohe atmospheric residue in slurry-bed hydrocracking, Database Caplus [Online] Chemical Abstracts Service, Database accession No. 2013:1445531 (2013).
Smith et al., Substitute Effects in Chemical Carcinogenesis: Methyl Derivatives of the Benzacridines, Journal of Hererocyclic Chemistry, vol. 16, No. 3, Apr. 1, 1979, pp. 421-425.
Buu-Hoï et al., Carcinogenic nitrogen compounds. XXXI. Benzacridines and other nitrogen heterocyclic derivatives of m-ethylaniline, Journal of the Chemical Society, Jan. 1, 1961, pp. 4836-4839.
Croisy-Delcey et al., Synthesis and Carcinogenic Activity of Oxidized Benzacridines: Potential Metabolites of the Strong Carcinogen 7-Methylbenz[c]acridine and of the Inactive Isomer 12-Methylbenz[a]acridine, Journal of Medicinal Chemistry, American Chemical Society, vol. 26, No. 2, Jan. 1, 1983, pp. 303-306.
Bergmann et al., Fluoro derivatives of polycyclic carcinogenic compounds, Database Caplus [Online] Chemical Abstracts Service, Database accession No. 1959:77800 (1959).

\* cited by examiner

COMPOUND AND AN ORGANIC SEMICONDUCTING LAYER, AN ORGANIC ELECTRONIC DEVICE AND A DISPLAY OR LIGHTING DEVICE COMPRISING THE SAME

CROSS REFERENCE TO RELATED APPLICATIONS

This application is a U.S. national phase application of PCT/EP2020/060978, filed Apr. 20, 2020, which claims priority to European Application No. 19170921.1, filed Apr. 24, 2019. The content of these applications is incorporated herein by reference.

The present invention relates to a compound as well as to an organic semiconducting layer comprising the same. The invention further relates to an organic electronic device comprising the organic semiconducting layer, respectively the compound. Furthermore, the invention is related to a display device or a lighting device comprising the organic electronic device.

BACKGROUND ART

Organic light-emitting diodes (OLEDs), which are self-emitting devices, have a wide viewing angle, excellent contrast, quick response, high brightness, excellent driving voltage characteristics, and color reproduction. A typical OLED includes an anode, a hole transport layer (HTL), an emission layer (EML), an electron transport layer (ETL), and a cathode, which are sequentially stacked on a substrate. In this regard, the HTL, the EML, and the ETL are thin films formed from organic and/or organometallic compounds.

When a voltage is applied to the anode and the cathode, holes injected from the anode electrode move to the EML, via the HTL, and electrons injected from the cathode electrode move to the EML, via the ETL. The holes and electrons recombine in the EML to generate excitons. When the excitons drop from an excited state to a ground state, light is emitted. The injection and flow of holes and electrons should be balanced, so that an OLED having the above-described structure has excellent efficiency.

However, there is still a need to improve the electronic properties of respective compounds for use in organic electronic devices, in particular for improving the performance thereof, and to provide respective organic electronic devices having improved performance. It is an particular aim of the present invention to improve the performance of top emission OLEDs, in particular with respect to lifetime and efficiency thereof.

It is, therefore, an object of the present invention to provide novel organic electronic devices and compounds for use therein overcoming drawbacks of the prior art, in particular to provide novel compounds having improved properties and being suitable to improve the lifetime and efficiency of organic electronic devices comprising the same, in particular when being used in an electron transport layer thereof.

This object is, first of all, achieved by a compound of Formula (I)

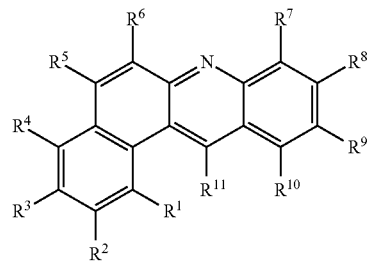

(I)

wherein one or two of $R^1$ to $R^{11}$ are independently a group G, wherein G is selected from the group consisting of substituted or unsubstituted $C_6$ to $C_{48}$ aryl, substituted or unsubstituted $C_2$ to $C_{42}$ heteroaryl, and substituted or unsubstituted alkenyl, substituted or unsubstituted $C_1$ to $C_{16}$ alkyl, substituted or unsubstituted $C_1$ to $C_{16}$ alkoxy, CN, F, deuterium, nitrile, amino, $P(=Y)(R^{12})_2$ with Y being O or S, wherein $R^{12}$ are independently selected from the group consisting of $C_1$ to $C_{16}$ alkyl, $C_1$ to $C_{16}$ alkoxy, $C_6$ to $C_{18}$ aryl and $C_3$ to $C_{25}$ heteroaryl;

the remaining $R^1$ to $R^{11}$ which are not G are H;

the one or two G may be attached to the benzoacridine moiety in Formula (I) via a direct bond or via a spacer unit;

the one or two spacer unit(s), if present, is/are independently selected from the group consisting of substituted or unsubstituted $C_6$ to $C_{18}$ arylene and substituted or unsubstituted $C_2$ to $C_{20}$ heteroarylene;

the one or more substituent(s) of $R^1$ to $R^{11}$ and/or the spacer unit(s), if present, are independently selected from the group consisting of $C_6$ to $C_{18}$ aryl, wherein it may be provided that adjacent $C_6$ to $C_{18}$ aryl substituents are linked with each other via a direct bond, $C_3$ to $C_{20}$ heteroaryl, $C_1$ to $C_{16}$ alkyl, D, F, $C_1$ to $C_{16}$ alkoxy, CN, CN-substituted $C_6$ to $C_{18}$ aryl, and $P(=Y)(R^{12})_2$ with Y being O or S, wherein $R^{12}$ is independently selected from the group consisting of $C_1$ to $C_{16}$ alkyl, $C_1$ to $C_{16}$ alkoxy, $C_6$ to $C_{18}$ aryl and $C_3$ to $C_{25}$ heteroaryl; and it is provided that if one of $R^9$ and $R^{11}$ is G, then the other one of $R^9$ and $R^{11}$ is H.

It was surprisingly found by the inventors that the inventive compounds are suitable to improve the performance of an organic electronic device comprising the same, in particular the performance of top emission OLEDs comprising the same in an electron transport layer thereof. In particular, it was observed that the performance of such devices can be improved with respect to lifetime and efficiency when using the inventive compounds.

In the following when reference is made to "benzoacridine" or "benzoacridine moiety", it is referred—if not being explicitly stated else—to the following benzo[a]acridine moiety

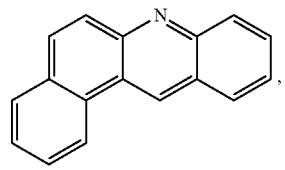 [SMILES: c1ccc2nc3ccc4ccccc4c3cc2c1]

i.e. the core element of formula (I) without the substituents $R^1$ to $R^{11}$.

According to the invention, it is provided that either one or two of $R^1$ to $R^{11}$ independent from each other represent a group G. The remaining $R^1$ to $R^{11}$ which do not represent the one or two groups G comprised in the formula (I) are H. That is, one or two group(s) G is/are attached to the benzoacridine moiety while the remaining positions of the benzoacridine moiety remain unsubstituted.

The one or two G may each independently be attached to the benzoacridine moiety of formula (I) either via a direct bond or via a spacer. In this regard, it may be provided that both G are attached to the benzoacridine moiety via a direct bond, that both of G are attached to the benzoacridine moiety via a spacer unit, or one of the two G groups is attached via a direct bond and the other group G is attached via a spacer unit. In this regard, a direct bond means a single bond between the benzoacridine moiety and the respective group $R^1$ to $R^{11}$. In case of using a spacer unit, the spacer unit is attached with one bond to the benzoacridine moiety and with another bond to the respective group $R^1$ to $R^{11}$.

It was further surprisingly found by the inventors that within the group of advantageous compounds referred to above (helpful for improving OLEDs in particular with respect to lifetime and efficiency thereof) certain compounds are particularly preferred, i.e. result in even more pronounced improvements regarding lifetime and/or efficiency. Respective embodiments will be described in the following. The inventors have further noted that the combination of two or more of the following embodiments may be particularly helpful for improving the relevant properties of organic electronic devices.

With respect to the inventive compound of formula (I), it may be provided that in case that $R^{11}$ is G one of $R^1$ to $R^{10}$ is also G, wherein the two G are selected independently from each other. That is, it may be provided that in case that $R^{11}$ is a group G, as defined herein, the possibility that all of the remaining $R^{11}$ to $R^{10}$ are selected as H may be excluded. In other words, it may be provided that if $R^{11}$ is G then two of $R^1$ to $R^{11}$ are independently a group G.

Additionally, it may be provided that in case that $R^{11}$ is G substituents on this group G are independently selected form the group consisting of D, F, CN, nitrile, amino $C_6$ to $C_{18}$ aryl, CN-substituted $C_6$ to $C_{18}$ aryl, $C_3$ to $C_{20}$ heteroaryl, CN, $C_1$ to $C_{16}$ alkyl, substituted or unsubstituted alkenyl, and substituted or unsubstituted $C_1$ to $C_{16}$ alkoxy. That is, in case that $R^{11}$ is G, it may be provided that the group G in the $R^{11}$ position does not contain any $P(=Y)(R^{12})_2$ groups, in particular no $PO(R^{12})_2$ groups. In other words, it may be excluded that the group G is a respective alkyl or aryl phosphine oxide group per se and it may also be excluded that the group G is substituted with one or more of the respective alkyl/aryl phosphine oxide groups.

Alternatively, it may be provided that if $R^{11}$ is $P(=Y)(R^{12})_2$ or $R^{11}$ is substituted with one or more groups of the formula $P(=Y)(R^{12})_2$ then the total number of groups G in formula (I) is 2. In other words, in such a case, it may be provided that besides $R^{11}$ one of the remaining $R^1$ to $R^{10}$ is selected as G, wherein the both G are selected independently from each other.

In another embodiment, it may be provided that $R^{11}$ is H.

Furthermore, it may be provided that one or two of $R^2$, $R^4$, $R^5$, $R^7$, $R^8$, and $R^{11}$ are G, alternatively one or two of $R^5$, $R^7$ and $R^8$ are G, alternatively $R^5$ is G.

Additionally, it may be provided that in case that two of $R^1$ to $R^{11}$ are G and $R^5$ is G, then one of $R^8$, $R^9$ or $R^{11}$ is the other G.

It may be provided that the spacer unit is independently a $C_6$ to $C_{12}$ aryl, alternatively phenylene or biphenylene.

In addition, it may be provided that G is independently selected from substituted or unsubstituted $C_6$ to $C_{18}$ aryl, substituted or unsubstituted $C_3$ to $C_{21}$ heteroaryl, or substituted alkenyl.

Furthermore, it may be provided that in case that G is heteroaryl, the heteroaryl is a N-containing heteroaryl.

Additionally, it may be provided that the one or two groups G is/are independently selected from the group consisting of phenyl, naphthyl, anthracenyl, phenanthryl, fluorenyl, spirobi[fluorenyl], fluoranthenyl, pyridinyl, bipyridinyl, pyrimidinyl, diazinyl, triazinyl, quinolinyl, quinazolinyl, benzimidazolyl, benzoacridinyl, dibenzoacridinyl, benzo[h]quinazolinyl, carbazolyl, carbolinyl, 4,5-diazacabazolyl, phenanthrolinyl, dibenzofuranyl, dimethylphosphineoxide, diphenylphosphineoxide, triphenylalkenyl, [1]benzotieno[3,2-d]pyrimidinyl,

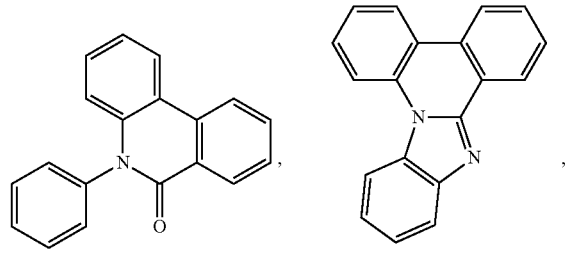 [SMILES: O=c1c2ccccc2c2ccccc2n1-c1ccccc1 ; c1ccc2c(c1)nc1c3ccccc3c3ccccc3n21]

wherein the respective groups may be substituted or unsubstituted.

Furthermore, it may be provided that the one or more substituent(s), if present on one or more or the groups $R^1$ to $R^{11}$ and/or the spacer unit(s), are independently selected from the group consisting of $C_6$ to $C_{12}$ aryl, $C_5$ to $C_{12}$ heteroaryl, CN-substituted $C_6$ to $C_{12}$ aryl, $C_6$ to $C_{12}$ aryl substituted with $P(=O)(R^{12})_2$ with $R^{12}$ being $C_1$ to $C_{12}$ alkyl or phenyl, $C_1$ to $C_5$ alkyl, CN, $P(=O)(R^{12})_2$ with $R^{12}$ being $C_1$ to $C_5$ alkyl or phenyl, preferably selected from the group consisting of phenyl, naphthyl, biphenyl, CN-substituted phenyl, pyridyl, CN, dibenzofuranyl, dimethylphosphineoxide-substituted phenyl, ethyl, methyl, dimethylphosphine oxide or diphenylphosphine oxide.

In accordance with the invention, the number of aromatic rings in the compound of formula (I) may be from 5 to 15, alternatively from 6 to 10.

The compound according to formula (I) may be represented by one of the following formulas 1 to 58

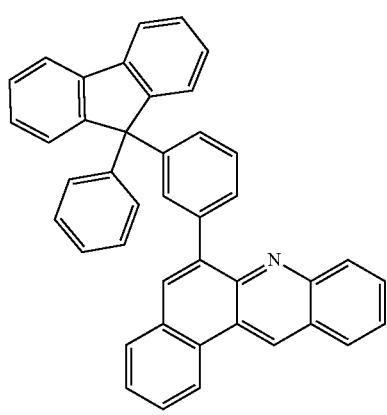

1

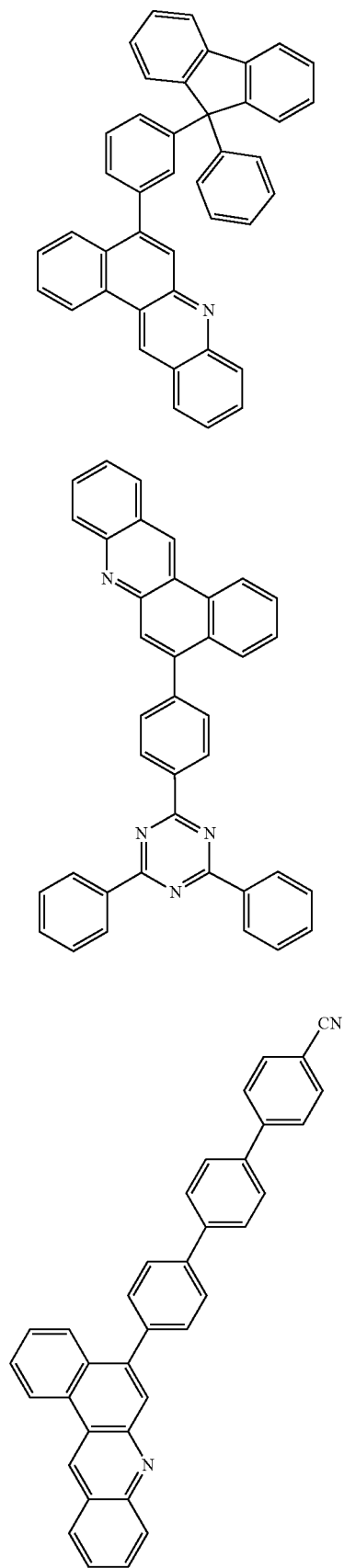
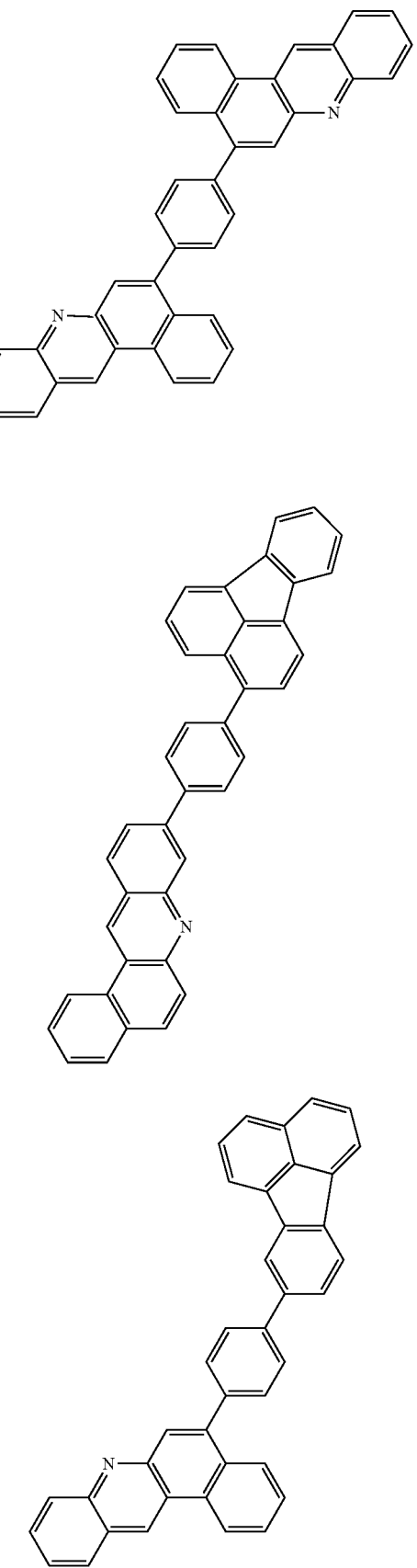

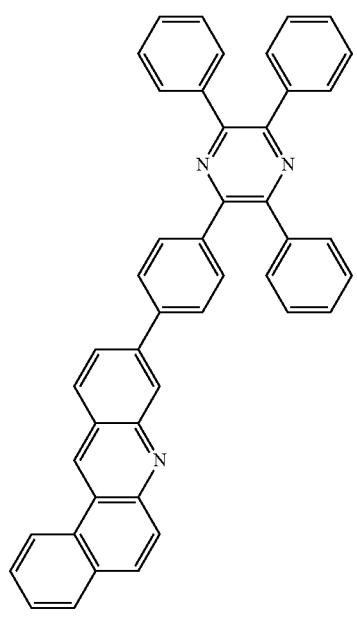
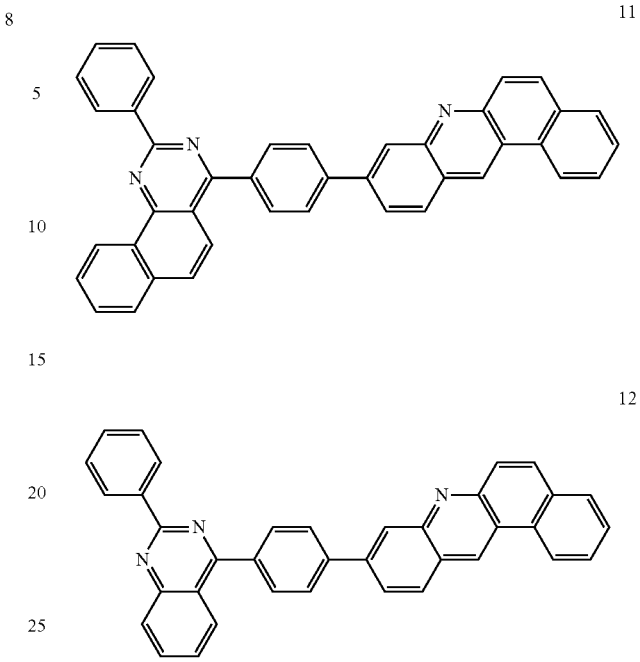
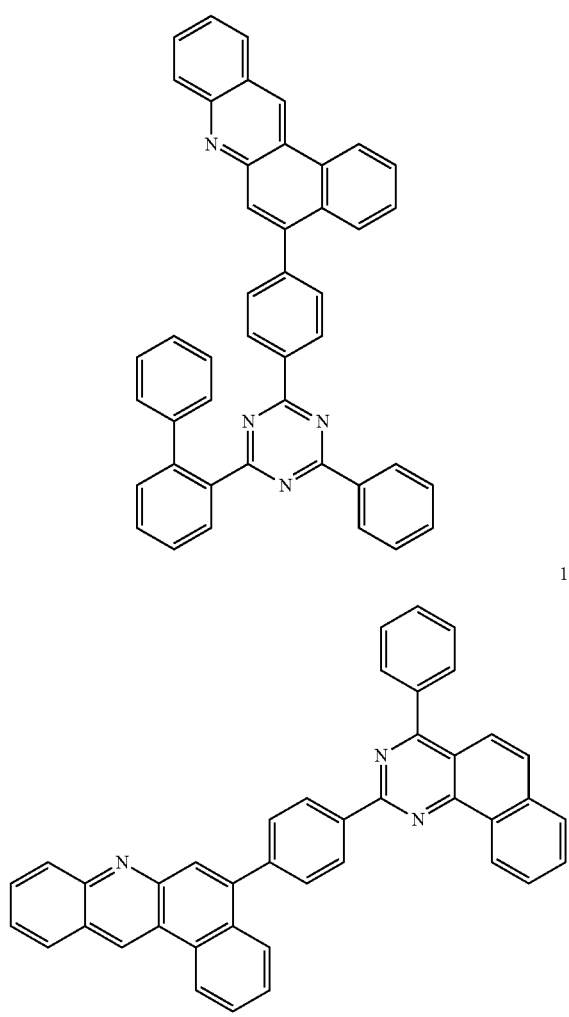
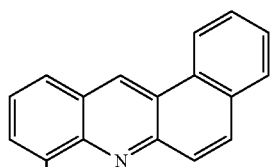
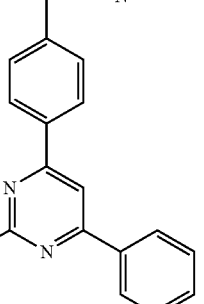

15
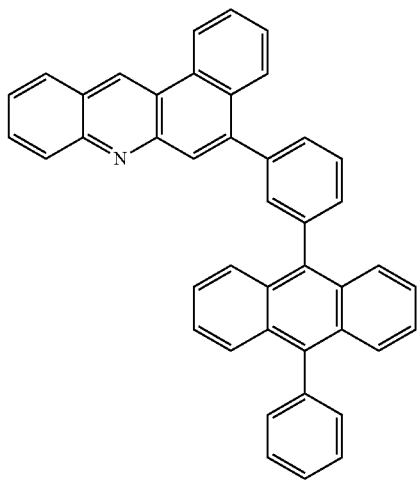
16
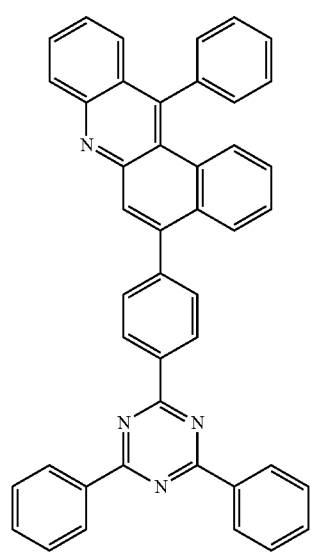
17
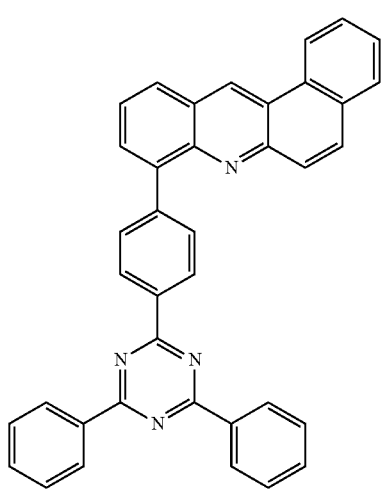
18
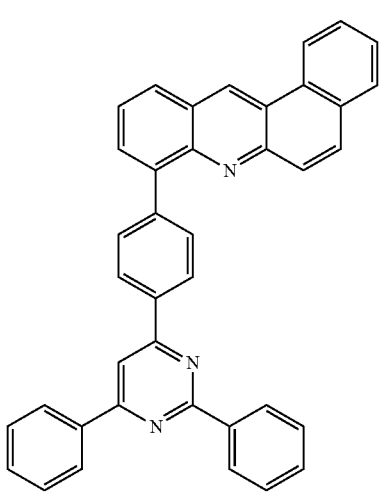
19
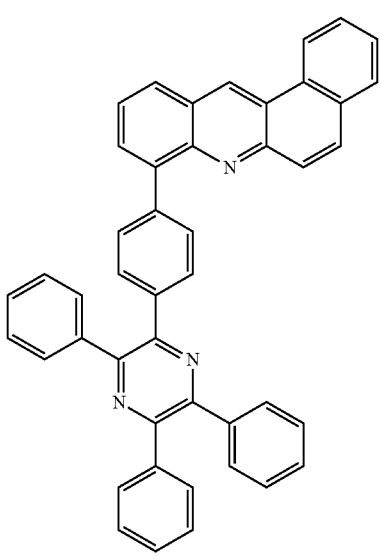
20
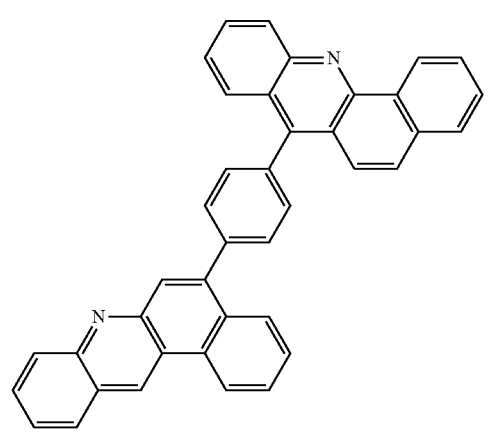

21
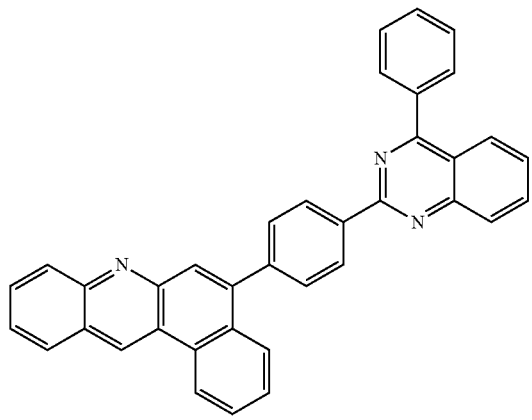
22
23
24
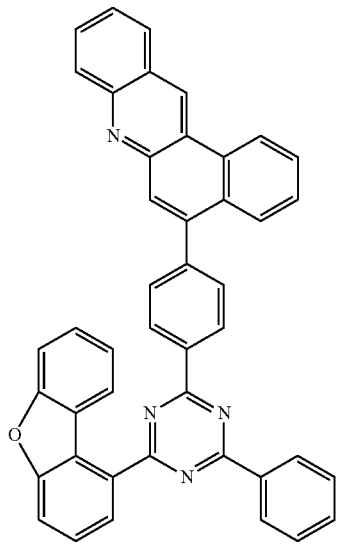
25
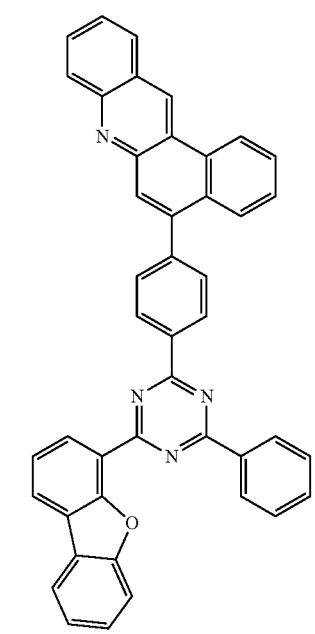
26
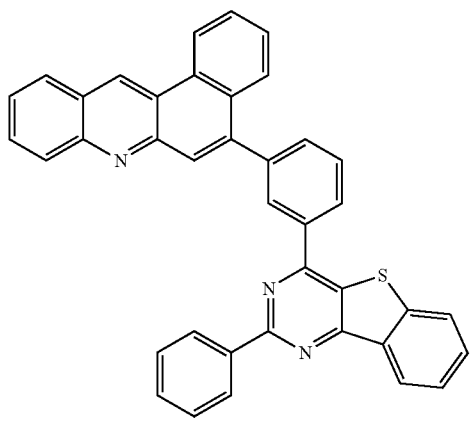

27
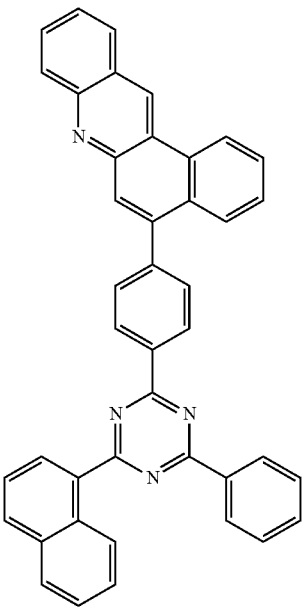
28
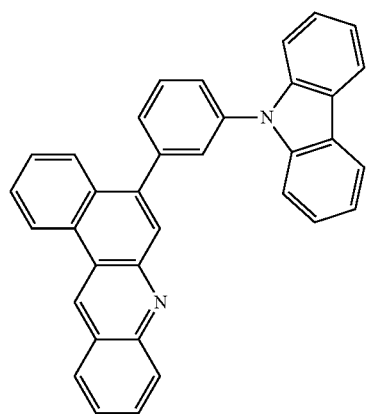
29
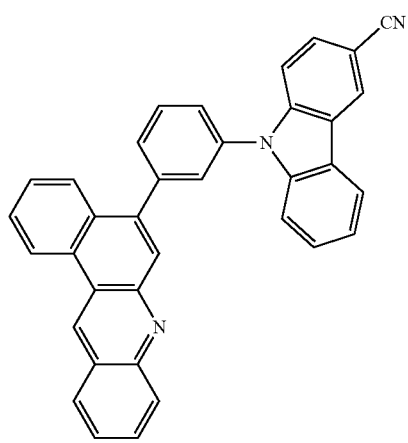
30
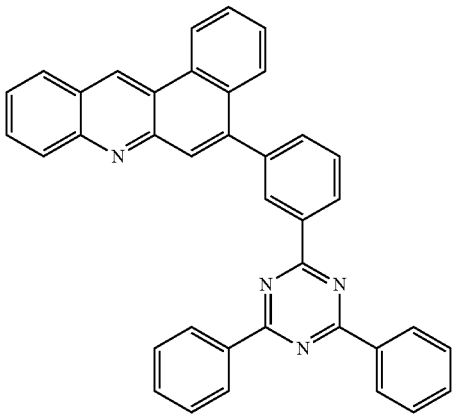
31
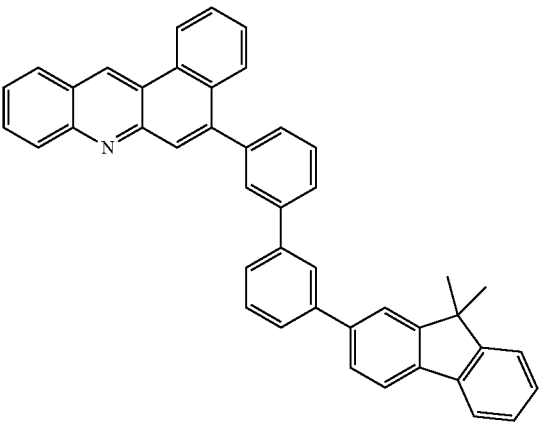
32

33
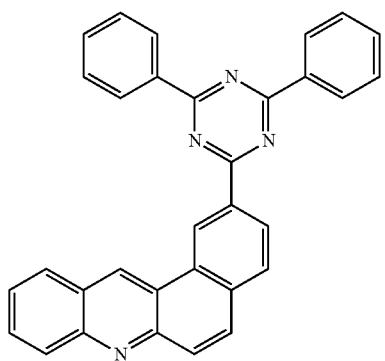
34
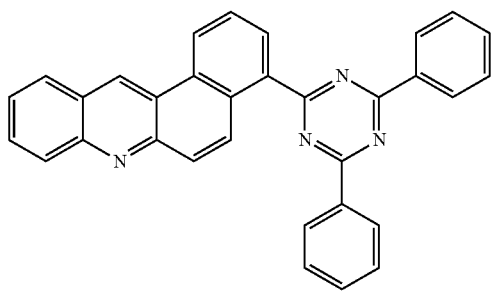
35
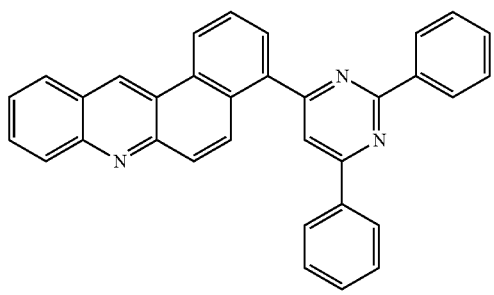
36
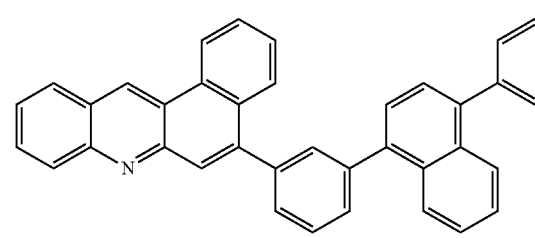
37
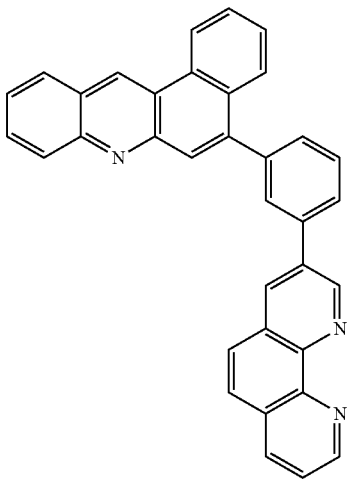
38
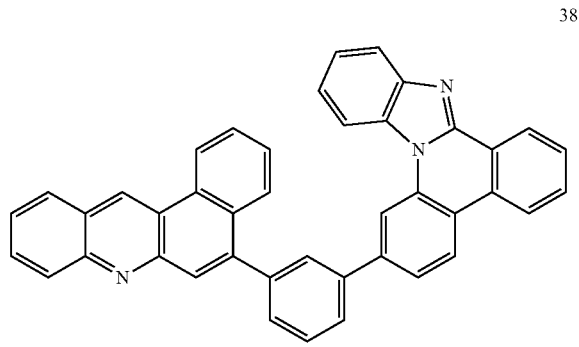
39
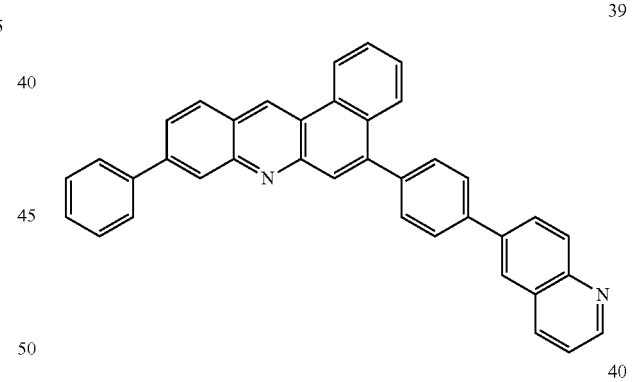
40
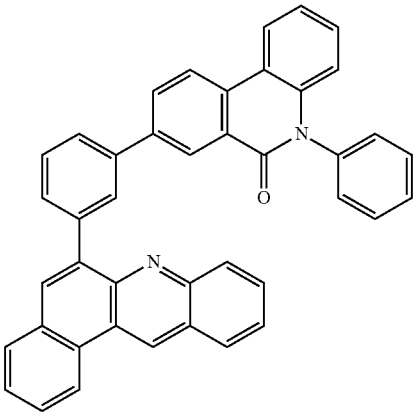

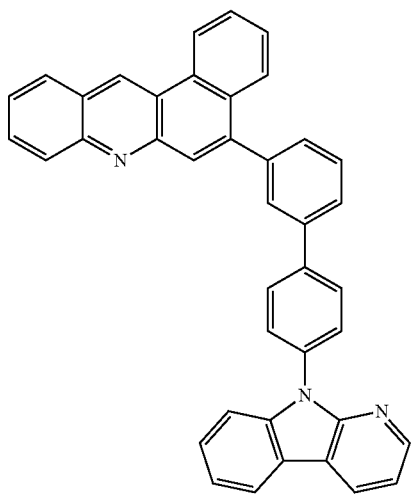
41
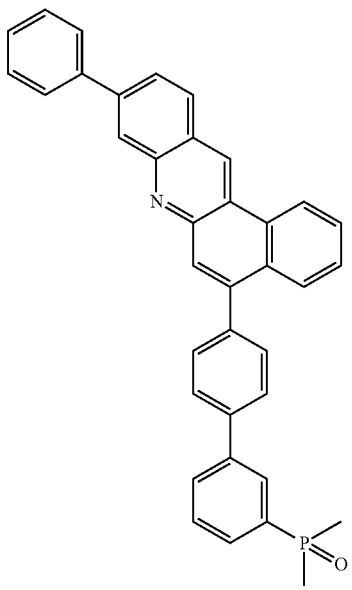
44
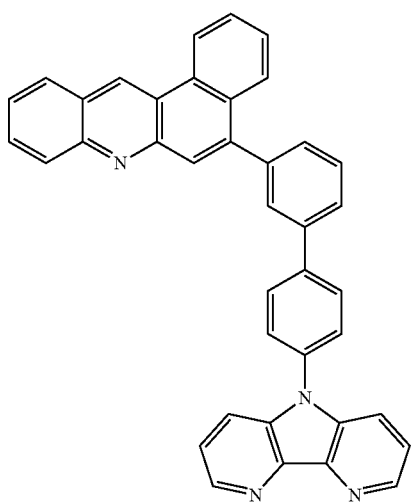
42
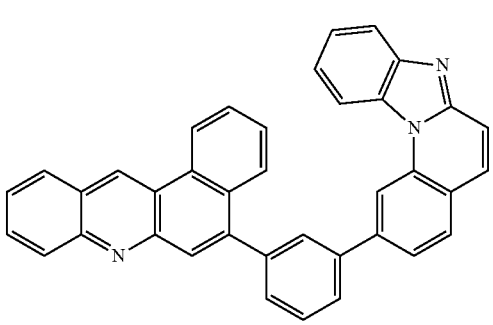
45
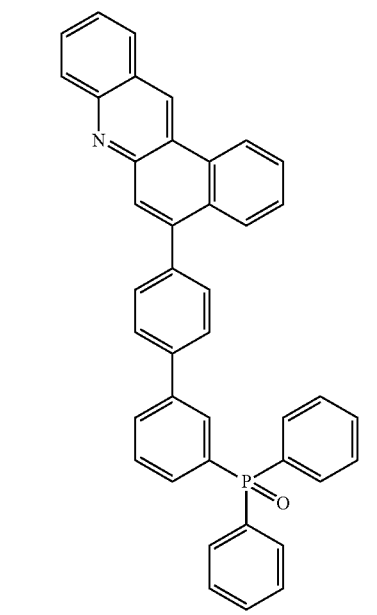
43
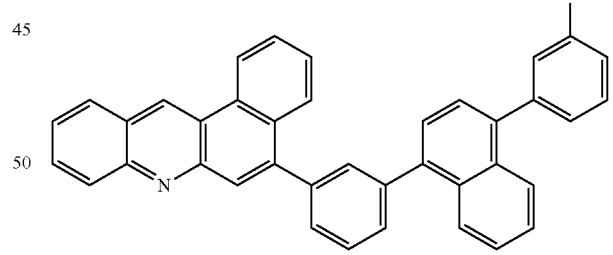
46
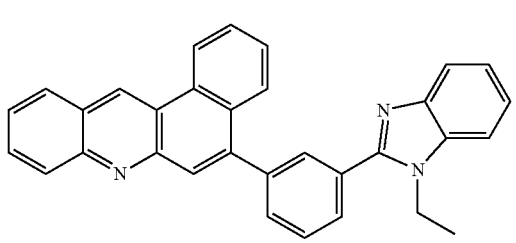
47

48
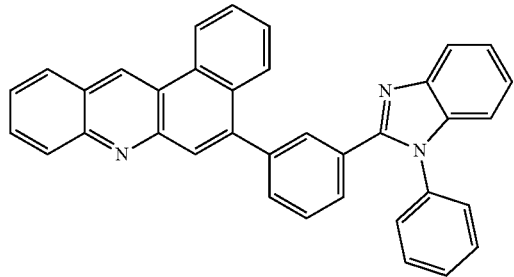
49
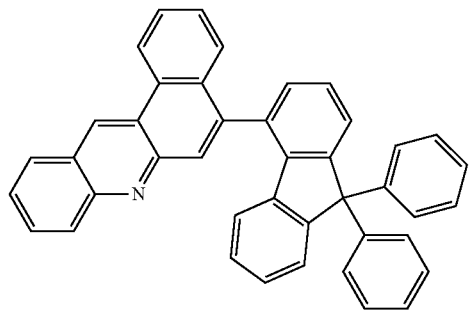
50
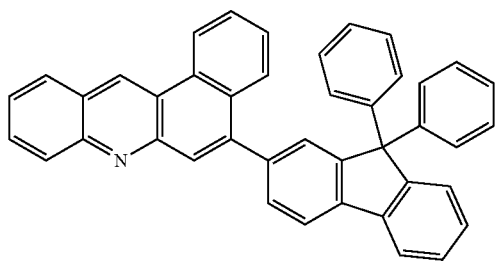
51
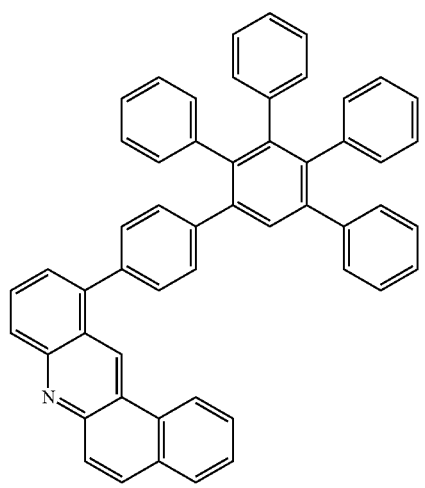
52
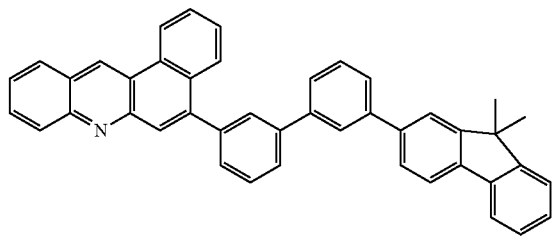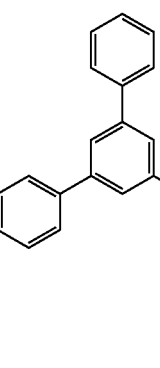
53
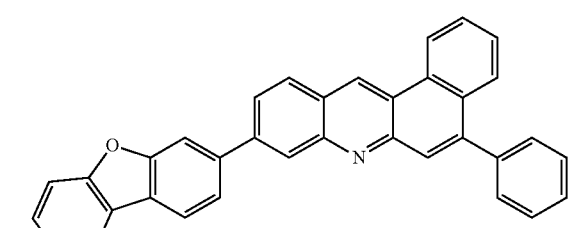
54
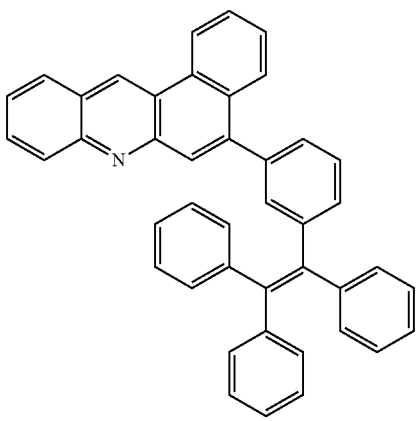
55
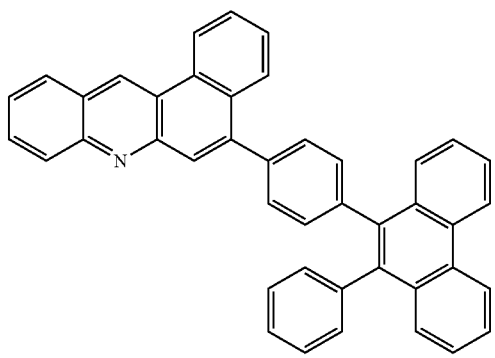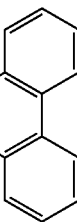
56

57

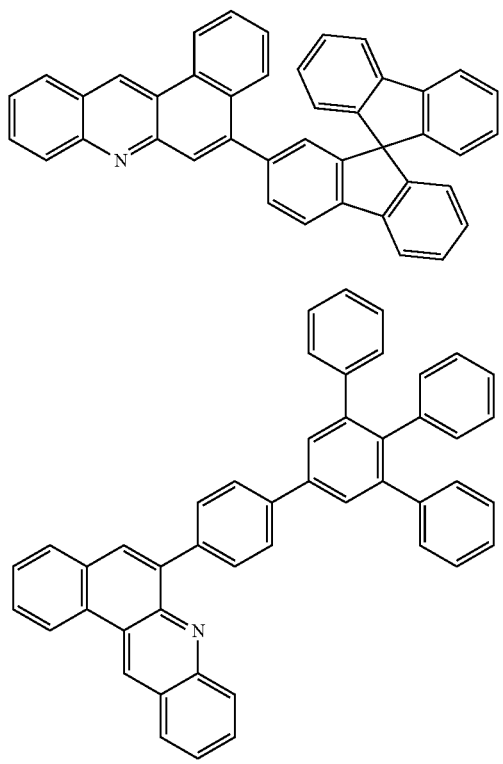

58

The object is further achieved by an organic semiconducting layer comprising the compound of formula (I) as defined herein in terms of the broadest definition thereof, in terms of embodiments or in terms of combinations thereof.

In this regard, it may be provided that the organic semiconducting layer consists of the compound of formula (I).

It may be provided that the organic semiconducting layer does not contain a dopant or an additive.

Alternatively, the organic semiconducting layer may comprise an n-type additive which may be selected from a metal, a metal salt or a metal complex.

The n-type additive may be an n-type dopant. The n-type dopant may be a reductive dopant in the sense that it donates an electron to the first or second matrix compound.

In regard, the metal may be selected from alkali metal, alkaline earth metal and transition metal which may be a rare earth metal. The metal salt may be the salt of an alkali metal, the salt of an alkaline earth metal or the salt of a rare earth metal. The alkali metal salt may be selected from the group consisting of LiF, LiCl, LiBr or LiI, alternatively may be LiF. The metal complex may be an organic alkali metal complex, alternatively an alkali metal complex, alternatively LiQ or alkali borate.

The organic semiconducting layer may further comprise at least one second matrix compound. This second matrix compound is not an n-type dopant or an n-type additive. This second matrix compound may be a charge transport material.

The organic semiconducting layer may be essentially non-emissive.

The object is further achieved by an organic electronic device comprising the inventive semiconducting layer.

It may be provided that the organic electronic device comprises a first electrode and a second electrode and that the organic semiconducting layer is arranged between the first electrode and the second electrode.

It may be provided that the organic electronic device comprises two emission layers and that the organic semiconducting layer is arranged between the two emission layers. In case that the organic electronic device comprises more than two emission layers, the organic semiconducting layer is arranged between (at least) two of them.

The organic electronic device may further comprise an auxiliary electron transport layer and the organic semiconducting layer may be arranged in direct contact with the auxiliary electron transport layer. The compound of formula (I) may be comprised in the auxiliary electron transport layer or, alternatively, the auxiliary electron transport layer may consist of the compound of formula (I).

The organic electronic device may comprise an emission layer and the semiconducting layer may be arranged in direct contact with the emission layer.

The organic electronic device may comprise an electron transport layer and the organic semiconducting layer may be arranged in direct contact with the electron transport layer.

The organic electronic device may comprise a cathode and the organic semiconducting layer may be arranged in direct contact with the cathode.

The object is further achieved by a display device comprising the inventive organic electronic device.

Finally, the object is achieved by a lighting device comprising the inventive organic electronic device.

Embodiments and combinations thereof referred to above with respect to the inventive compound are also embodiments for realizing the organic semiconducting layer, the organic electronic device, the display device or the lighting device as disclosed herein.

Further Layers

In accordance with the invention, the organic electronic device may comprise, besides the layers already mentioned above, further layers. Exemplary embodiments of respective layers are described in the following:

Substrate

The substrate may be any substrate that is commonly used in manufacturing of, electronic devices, such as organic light-emitting diodes. If light is to be emitted through the substrate, the substrate shall be a transparent or semitransparent material, for example a glass substrate or a transparent plastic substrate. If light is to be emitted through the top surface, the substrate may be both a transparent as well as a non-transparent material, for example a glass substrate, a plastic substrate, a metal substrate or a silicon substrate.

Anode Electrode

Either a first electrode or a second electrode comprised in the inventive organic electronic device may be an anode electrode. The anode electrode may be formed by depositing or sputtering a material that is used to form the anode electrode. The material used to form the anode electrode may be a high work-function material, so as to facilitate hole injection. The anode material may also be selected from a low work function material (i.e. aluminum). The anode electrode may be a transparent or reflective electrode. Transparent conductive oxides, such as indium tin oxide (ITO), indium zinc oxide (IZO), tin-dioxide ($SnO_2$), aluminum zinc oxide (AlZO) and zinc oxide (ZnO), may be used to form the anode electrode. The anode electrode may also be formed using metals, typically silver (Ag), gold (Au), or metal alloys.

Hole Injection Layer

A hole injection layer (HIL) may be formed on the anode electrode by vacuum deposition, spin coating, printing, casting, slot-die coating, Langmuir-Blodgett (LB) deposition, or the like. When the HIL is formed using vacuum deposition, the deposition conditions may vary according to the compound that is used to form the HIL, and the desired structure and thermal properties of the HIL. In general, however, conditions for vacuum deposition may include a deposition temperature of 100° C. to 500° C., a pressure of 10-8 to 10-3 Torr (1 Torr equals 133.322 Pa), and a deposition rate of 0.1 to 10 nm/sec.

When the HIL is formed using spin coating or printing, coating conditions may vary according to the compound that is used to form the HIL, and the desired structure and thermal properties of the HIL. For example, the coating conditions may include a coating speed of about 2000 rpm to about 5000 rpm, and a thermal treatment temperature of about 80° C. to about 200° C. Thermal treatment removes a solvent after the coating is performed.

The HIL may be formed of any compound that is commonly used to form a HIL. Examples of compounds that may be used to form the HIL include a phthalocyanine compound, such as copper phthalocyanine (CuPc), 4,4',4"-tris(3-methylphenylphenylamino) triphenylamine (m-MTDATA), MTDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline/poly(4-styrenesulfonate (PANI/PSS).

The HIL may comprise or consist of p-type dopant and the p-type dopant may be selected from tetrafluoro-tetracyanoquinonedimethane (F4TCNQ), 2,2'-(perfluoronaphthalen-2,6-diylidene) dimalononitrile or 2,2',2"-(cyclopropane-1,2,3-triylidene)tris(2-(p-cyanotetrafluorophenyl)acetonitrile) but not limited hereto. The HIL may be selected from a hole-transporting matrix compound doped with a p-type dopant. Typical examples of known doped hole transport materials are: copper phthalocyanine (CuPc), which HOMO level is approximately −5.2 eV, doped with tetrafluoro-tetracyanoquinonedimethane (F4TCNQ), which LUMO level is about −5.2 eV; zinc phthalocyanine (ZnPc) (HOMO=−5.2 eV) doped with F4TCNQ; α-NPD (N,N'-Bis(naphthalen-1-yl)-N,N'-bis(phenyl)-benzidine) doped with F4TCNQ. α-NPD doped with 2,2'-(perfluoronaphthalen-2,6-diylidene) dimalononitrile. The p-type dopant concentrations can be selected from 1 to 20 wt.-%, more preferably from 3 wt.-% to 10 wt.-%.

The thickness of the HIL may be in the range from about 1 nm to about 100 nm, and for example, from about 1 nm to about 25 nm. When the thickness of the HIL is within this range, the HIL may have excellent hole injecting characteristics, without a substantial penalty in driving voltage.

Hole Transport Layer

A hole transport layer (HTL) may be formed on the HIL by vacuum deposition, spin coating, slot-die coating, printing, casting, Langmuir-Blodgett (LB) deposition, or the like. When the HTL is formed by vacuum deposition or spin coating, the conditions for deposition and coating may be similar to those for the formation of the HIL. However, the conditions for the vacuum or solution deposition may vary, according to the compound that is used to form the HTL.

The HTL may be formed of any compound that is commonly used to form a HTL. Compounds that can be suitably used are disclosed for example in Yasuhiko Shirota and Hiroshi Kageyama, Chem. Rev. 2007, 107, 953-1010 and incorporated by reference. Examples of the compound that may be used to form the HTL are: carbazole derivatives, such as N-phenylcarbazole or polyvinylcarbazole; benzidine derivatives, such as N,N'-bis(3-methylphenyl)-N,N-diphenyl-[1,1-biphenyl]-4,4'-diamine (TPD), or N,N'-di(naphthalen-1-yl)-N,N'-diphenyl benzidine (alpha-NPD); and triphenylamine-based compound, such as 4,4',4"-tris(N-carbazolyl)triphenylamine (TCTA). Among these compounds, TCTA can transport holes and inhibit excitons from being diffused into the EML.

The thickness of the HTL may be in the range of about 5 nm to about 250 nm, preferably, about 10 nm to about 200 nm, further about 20 nm to about 190 nm, further about 40 nm to about 180 nm, further about 60 nm to about 170 nm, further about 80 nm to about 160 nm, further about 100 nm to about 160 nm, further about 120 nm to about 140 nm. A preferred thickness of the HTL may be 170 nm to 200 nm.

When the thickness of the HTL is within this range, the HTL may have excellent hole transporting characteristics, without a substantial penalty in driving voltage.

Electron Blocking Layer

The function of an electron blocking layer (EBL) is to prevent electrons from being transferred from an emission layer to the hole transport layer and thereby confine electrons to the emission layer. Thereby, efficiency, operating voltage and/or lifetime are improved. Typically, the electron blocking layer comprises a triarylamine compound. The triarylamine compound may have a LUMO level closer to vacuum level than the LUMO level of the hole transport layer. The electron blocking layer may have a HOMO level that is further away from vacuum level compared to the HOMO level of the hole transport layer. The thickness of the electron blocking layer may be selected between 2 and 20 nm.

If the electron blocking layer has a high triplet level, it may also be described as triplet control layer.

The function of the triplet control layer is to reduce quenching of triplets if a phosphorescent green or blue emission layer is used. Thereby, higher efficiency of light emission from a phosphorescent emission layer can be achieved. The triplet control layer is selected from triarylamine compounds with a triplet level above the triplet level of the phosphorescent emitter in the adjacent emission layer. Suitable compounds for the triplet control layer, in particular the triarylamine compounds, are described in EP 2 722 908 A1.

Emission Layer (EML)

The EML may be formed on the HTL by vacuum deposition, spin coating, slot-die coating, printing, casting, LB deposition, or the like. When the EML is formed using vacuum deposition or spin coating, the conditions for deposition and coating may be similar to those for the formation of the HIL. However, the conditions for deposition and coating may vary, according to the compound that is used to form the EML.

It may be provided that the emission layer does not comprise the compound of Formula (I).

The emission layer (EML) may be formed of a combination of a host and an emitter dopant. Example of the host are Alq3, 4,4'-N,N'-dicarbazole-biphenyl (CBP), poly(n-vinylcarbazole) (PVK), 9,10-di(naphthalene-2-yl)anthracene (ADN), 4,4',4"-tris(carbazol-9-yl)-triphenylamine (TCTA), 1,3,5-tris(N-phenylbenzimidazole-2-yl)benzene (TPBI), 3-tert-butyl-9,10-di-2-naphthylanthracenee (TBADN), distyrylarylene (DSA) and bis(2-(2-hydroxyphenyl)benzothiazolate)zinc (Zn(BTZ)2).

The emitter dopant may be a phosphorescent or fluorescent emitter. Phosphorescent emitters and emitters which emit light via a thermally activated delayed fluorescence (TADF) mechanism may be preferred due to their higher efficiency. The emitter may be a small molecule or a polymer.

Examples of red emitter dopants are PtOEP, Ir(piq)3, and Btp2Ir(acac), but are not limited thereto. These compounds are phosphorescent emitters, however, fluorescent red emitter dopants could also be used.

Examples of phosphorescent green emitter dopants are Ir(ppy)3 (ppy=phenylpyridine), Ir(ppy)2(acac), Ir(mpyp)3.

Examples of phosphorescent blue emitter dopants are F2Irpic, (F2ppy)2Ir(tmd) and Ir(dfppz)3 and ter-fluorene. 4,4'-bis(4-diphenyl amiostyryl)biphenyl (DPAVBi), 2,5,8,11-tetra-tert-butyl perylene (TBPe) are examples of fluorescent blue emitter dopants.

The amount of the emitter dopant may be in the range from about 0.01 to about 50 parts by weight, based on 100 parts by weight of the host. Alternatively, the emission layer may consist of a light-emitting polymer. The EML may have a thickness of about 10 nm to about 100 nm, for example, from about 20 nm to about 60 nm. When the thickness of the EML is within this range, the EML may have excellent light emission, without a substantial penalty in driving voltage.

Hole Blocking Layer (HBL)

A hole blocking layer (HBL) may be formed on the EML, by using vacuum deposition, spin coating, slot-die coating, printing, casting, LB deposition, or the like, in order to prevent the diffusion of holes into the ETL. When the EML comprises a phosphorescent dopant, the HBL may have also a triplet exciton blocking function. The hole blocking layer may be the inventive organic semiconducting layer comprising or consisting of the inventive compound represented by the general Formula (I) as defined above.

The HBL may also be named auxiliary electron transport layer or a-ETL and electron transport layer 1 or ETL-1.

The HBL of the organic electronic device may comprise the compound represented by general Formula (I). Alternatively, the HBL may consist of the compound of formula (I).

When the HBL is formed using vacuum deposition or spin coating, the conditions for deposition and coating may be similar to those for the formation of the HIL. However, the conditions for deposition and coating may vary, according to the compound that is used to form the HBL. Any compound that is commonly used to form a HBL may be used. Examples of compounds for forming the HBL include oxadiazole derivatives, triazole derivatives, and phenanthroline derivatives.

The HBL may have a thickness in the range from about 5 nm to about 100 nm, for example, from about 10 nm to about 30 nm. When the thickness of the HBL is within this range, the HBL may have excellent hole-blocking properties, without a substantial penalty in driving voltage.

Electron Transport Layer (ETL)

The OLED according to the present invention may comprise an electron transport layer (ETL). In accordance with one preferred embodiment of the invention, the electron transport layer may be the inventive organic semiconducting layer comprising the inventive compound represented by the general Formula (I) as defined herein.

In an embodiment the ETL may consist of a compound of Formula (I).

According to various embodiments the OLED may comprise an electron transport layer or an electron transport layer stack comprising at least a first electron transport layer and at least a second electron transport layer.

By suitably adjusting energy levels of particular layers of the ETL, the injection and transport of the electrons may be controlled, and the holes may be efficiently blocked. Thus, the OLED may have long lifetime.

The electron transport layer of the organic electronic device may comprise the compound represented by general Formula (I) as defined above as the organic electron transport matrix (ETM) material which can also be referred to as a matrix compound. The electron transport layer may comprise, besides or instead of the compound represented by the general Formula (I), further ETM materials known in the art. In one embodiment the electron transport layer comprises besides of the compound represented by the general Formula (I), one further ETM material which is referred to as a second matrix compound. Likewise, the electron transport layer may comprise as the only electron transport matrix material the compound represented by general Formula (I). In case that the inventive organic electronic device comprises more than one electron transport layers, the compound represented by the general Formula (I) may be comprised in only one of the electron transport layers, in more than one of the electron transport layers or in all of the electron transport layers. In accordance with the invention, the electron transport layer may comprise, besides the ETM material, at least one additive as defined below.

Further, the organic semiconducting layer may comprise one or more n-type additives. The additive may be an n-type dopant. The additive can be alkali metal, alkali metal compound, alkaline earth metal, alkaline earth metal compound, transition metal, transition metal compound or a rare earth metal. In another embodiment, the metal can be one selected from a group consisting of Li, Na, K, Rb, Cs, Mg, Ca, Sr, Ba, La, Ce, Sm, Eu, Tb, Dy, and Yb. In another embodiment, the n-type dopant can be one selected from a group consisting of Cs, K, Rb, Mg, Na, Ca, Sr, Eu and Yb. In an embodiment the alkali metal compound may be 8-Hydroxyquinolinolato-lithium (LiQ), Lithium tetra(1H-pyrazol-1-yl)borate or Lithium 2-(diphenylphosphoryl)phenolate. Suitable compounds for the ETM (which may be used in addition to the inventive compound represented by the general Formula (I) as defined above) are not particularly limited. In one embodiment, the electron transport matrix compounds consist of covalently bound atoms. Preferably, the electron transport matrix compound comprises a conjugated system of at least 6, more preferably of at least 10 delocalized electrons. In one embodiment, the conjugated system of delocalized electrons may be comprised in aromatic or heteroaromatic structural moieties, as disclosed e.g. in documents EP 1 970 371 A1 or WO 2013/079217 A1.

According to another aspect of the present invention organic semiconducting layer may comprise one or more alkali metal salt and alkali metal organic complex the alkali metal salt is selected from the group comprising LiF, LiCl, LiBr or LiI, and preferably LiF;

the alkali metal organic complex is selected from the group comprising a lithium quinolinolate, lithium borate, lithium phenolate, lithium pyridinolate or comprises a lithium with a Schiff base ligand;

preferably the lithium quinolinolate complex has the formula IV, V or VI:

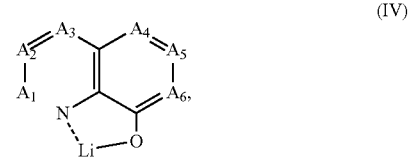

(IV)

(V)

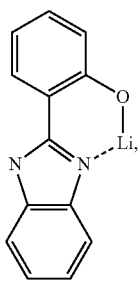

(VI)

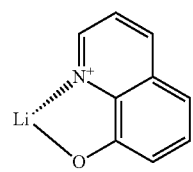

wherein

A₁ to A₆ are same or independently selected from CH, CR, N, O;

R is same or independently selected from hydrogen, halogen, alkyl or aryl or heteroaryl with 1 to 20 carbon atoms; and more preferred A1 to A6 are CH;

preferably the borate based organic ligand is a tetra(1H-pyrazol-1-yl)borate;

preferably the phenolate is a 2-(pyridin-2-yl)phenolate, a 2-(diphenylphosphoryl)phenolate, an imidazol phenolates, or 2-(pyridin-2-yl)phenolate and more preferred 2-(1-phenyl-1H-benzo[d]imidazol-2-yl)phenolate;

preferably the pyridinolate is a 2-(diphenylphosphoryl) pyridin-3-olate, preferably the lithium Schiff base has the structure 100, 101, 102 or 103:

100

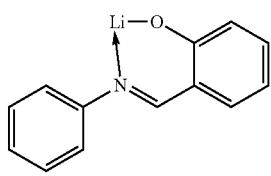

101

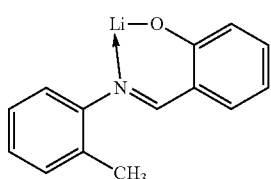

102

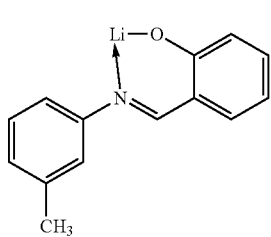

103

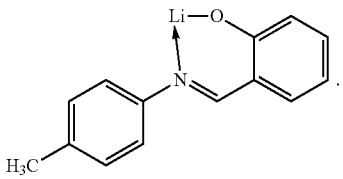

According to another aspect of the present invention, the OLED may comprise an electron transport layer or an electron transport layer stack comprising at least a first electron transport layer and at least a second electron transport layer wherein the first first electron transport layer may comprise the compound represented by general Formula (I).

Electron Injection Layer (EIL)

An optional EIL, which may facilitates injection of electrons from the cathode, may be formed on the ETL, preferably directly on the electron transport layer. Examples of materials for forming the EIL include lithium 8-hydroxyquinolinolate (LiQ), LiF, NaCl, CsF, Li2O, BaO, Ca, Ba, Yb, Mg which are known in the art. Deposition and coating conditions for forming the EIL are similar to those for formation of the HIL, although the deposition and coating conditions may vary, according to the material that is used to form the EIL. The EIL may be the organic semiconducting layer comprising the compound of Formula (I).

The thickness of the EIL may be in the range from about 0.1 nm to about 10 nm, for example, in the range from about 0.5 nm to about 9 nm. When the thickness of the EIL is within this range, the EIL may have satisfactory electron-injecting properties, without a substantial penalty in driving voltage.

Cathode Electrode

The cathode electrode is formed on the EIL if present. The cathode electrode may be formed of a metal, an alloy, an electrically conductive compound, or a mixture thereof. The cathode electrode may have a low work function. For example, the cathode electrode may be formed of lithium (Li), magnesium (Mg), aluminum (Al), aluminum (Al)-lithium (Li), calcium (Ca), barium (Ba), ytterbium (Yb), magnesium (Mg)-indium (In), magnesium (Mg)-silver (Ag), or the like. Alternatively, the cathode electrode may be formed of a transparent conductive oxide, such as ITO or IZO.

The thickness of the cathode electrode may be in the range from about 5 nm to about 1000 nm, for example, in the range from about 10 nm to about 100 nm. When the thickness of the cathode electrode is in the range from about 5 nm to about 50 nm, the cathode electrode may be transparent or semitransparent even if formed from a metal or metal alloy.

It is to be understood that the cathode electrode is not part of an electron injection layer or the electron transport layer.

Charge Generation Layer/Hole Generating Layer

The charge generation layer (CGL) may comprise a p-type and an n-type layer. An interlayer may be arranged between the p-type layer and the n-type layer.

Typically, the charge generation layer is a pn junction joining an n-type charge generation layer (electron generating layer) and a hole generating layer. The n-side of the pn junction generates electrons and injects them into the layer which is adjacent in the direction to the anode. Analogously, the p-side of the p-n junction generates holes and injects them into the layer which is adjacent in the direction to the cathode.

Charge generating layers are used in tandem devices, for example, in tandem OLEDs comprising, between two electrodes, two or more emission layers. In a tandem OLED comprising two emission layers, the n-type charge generation layer provides electrons for the first light emission layer arranged near the anode, while the hole generating layer provides holes to the second light emission layer arranged between the first emission layer and the cathode.

Suitable matrix materials for the hole generating layer may be materials conventionally used as hole injection and/or hole transport matrix materials. Also, p-type dopant used for the hole generating layer can employ conventional materials. For example, the p-type dopant can be one selected from a group consisting of tetrafluore-7,7,8,8-tetracyanoquinodimethane (F4-TCNQ), derivatives of tetracyanoquinodimethane, radialene derivatives, iodine, FeCl3, FeF3, and SbCl5. Also, the host can be one selected from a group consisting of N,N'-di(naphthalen-1-yl)-N,N-diphenyl-benzidine (NPB), N,N'-diphenyl-N,N'-bis(3-methylphenyl)-1,1-biphenyl-4,4'-diamine (TPD) and N,N',N'-tetranaphthyl-benzidine (TNB). The p-type charge generation layer may consist of CNHAT.

The n-type charge generating layer may be the layer comprising the compound of Formula (I). The n-type charge generation layer can be layer of a neat n-type dopant, for example of an electropositive metal, or can consist of an organic matrix material doped with the n-type dopant. In one embodiment, the n-type dopant can be alkali metal, alkali metal compound, alkaline earth metal, alkaline earth metal compound, a transition metal, a transition metal compound or a rare earth metal. In another embodiment, the metal can be one selected from a group consisting of Li, Na, K, Rb, Cs, Mg, Ca, Sr, Ba, La, Ce, Sm, Eu, Tb, Dy, and Yb. More specifically, the n-type dopant can be one selected from a group consisting of Cs, K, Rb, Mg, Na, Ca, Sr, Eu and Yb. Suitable matrix materials for the electron generating layer may be the materials conventionally used as matrix materials for electron injection or electron transport layers. The matrix material can be for example one selected from a group consisting of triazine compounds, hydroxyquinoline derivatives like tris(8-hydroxyquinoline)aluminum, benzazole derivatives, and silole derivatives.

The hole generating layer is arranged in direct contact to the n-type charge generation layer.

Organic Electronic Device

An organic electronic device according to the invention comprises an organic semiconducting layer comprising a compound according to Formula (I).

An organic electronic device according to one embodiment may include a substrate, an anode layer, an organic semiconducting layer comprising a compound of Formula (I) and a cathode layer.

An organic electronic device according to one embodiment comprises at least one organic semiconducting layer comprising at least one compound of Formula (I), at least one anode layer, at least one cathode layer and at least one emission layer, wherein the organic semiconducting layer is preferably arranged between the emission layer and the cathode layer.

An organic light-emitting diode (OLED) according to the invention may include an anode, a hole transport layer (HTL), an emission layer (EML), an electron transport layer (ETL) comprising at least one compound of Formula (I), and a cathode, which are sequentially stacked on a substrate. In this regard, the HTL, the EML, and the ETL are thin films formed from organic compounds.

An organic electronic device according to one embodiment can be a light emitting device, thin film transistor, a battery, a display device or a photovoltaic cell, and preferably a light emitting device.

According to another aspect of the present invention, there is provided a method of manufacturing an organic electronic device, the method using:
  at least one deposition source, preferably two deposition sources and more preferred at least three deposition sources.

The methods for deposition that can be suitable comprise:
  deposition via vacuum thermal evaporation;
  deposition via solution processing, preferably the processing is selected from spin-coating printing, casting; and/or
  slot-die coating.

According to various embodiments of the present invention, there is provided a method using:
  a first deposition source to release the compound of Formula (I) according to the invention, and
  a second deposition source to release the n-type additive which may be selected from a metal, a metal salt or an alkali or alkaline earth metal complex; alternatively an organic alkali or alkaline earth metal complex; alternatively 8-hydroxyquinolinolato lithium or alkali borate;
the method comprising the steps of forming the organic semiconducting layer; whereby for an organic light-emitting diode (OLED):
  the organic semiconducting layer is formed by releasing the compound of Formula (I) according to the invention from the first deposition source and an n-type additive which may be selected from a metal, a metal salt or an alkali or alkaline earth metal complex; alternatively an organic alkali or alkaline earth metal complex; alternatively 8-hydroxyquinolinolato lithium or alkali borate, from the second deposition source.

According to various embodiments of the present invention, the method may further include forming on the anode electrode, an emission layer and at least one layer selected from the group consisting of forming a hole injection layer, forming a hole transport layer, or forming a hole blocking layer, between the anode electrode and the first electron transport layer.

According to various embodiments of the present invention, the method may further include the steps for forming an organic light-emitting diode (OLED), wherein
  on a substrate a first anode electrode is formed,
  on the first anode electrode an emission layer is formed,
  on the emission layer an electron transport layer stack is formed, optionally a hole blocking layer is formed on the emission layer and an organic semiconducting layer is formed,
  and finally a cathode electrode is formed,
  optional a hole injection layer, a hole transport layer, and a hole blocking layer, formed in that order between the first anode electrode and the emission layer,
  optional an electron injection layer is formed between the organic semiconducting layer and the cathode electrode.

According to various embodiments of the present invention, the method may further comprise forming an electron injection layer on the organic semiconducting layer. However, according to various embodiments of the OLED of the present invention, the OLED may not comprise an electron injection layer.

According to various embodiments, the OLED may have the following layer structure, wherein the layers having the following order:

anode, hole injection layer, first hole transport layer, second hole transport layer, emission layer, optional hole blocking layer, organic semiconducting layer comprising a compound of Formula (I) according to the invention, optional electron injection layer, and cathode.

According to another aspect of the invention, it is provided an electronic device comprising at least one organic light emitting device according to any embodiment described throughout this application, preferably, the electronic device comprises the organic light emitting diode in one of embodiments described throughout this application. More preferably, the electronic device is a display device.

In one embodiment, the organic electronic device according to the invention comprising an organic semiconducting layer comprising a compound according to Formula (I) may further comprise a layer comprising a radialene compound and/or a quinodimethane compound.

In one embodiment, the radialene compound and/or the quinodimethane compound may be substituted with one or more halogen atoms and/or with one or more electron withdrawing groups. Electron withdrawing groups can be selected from nitrile groups, halogenated alkyl groups, alternatively from perhalogenated alkyl groups, alternatively from perfluorinated alkyl groups. Other examples of electron withdrawing groups may be acyl, sulfonyl groups or phosphoryl groups.

Alternatively, acyl groups, sulfonyl groups and/or phosphoryl groups may comprise halogenated and/or perhalogenated hydrocarbyl. In one embodiment, the perhalogenated hydrocarbyl may be a perfluorinated hydrocarbyl. Examples of a perfluorinated hydrocarbyl can be perfluormethyl, perfluorethyl, perfluorpropyl, perfluorisopropyl, perfluorobutyl, perfluorophenyl, perfluorotolyl; examples of sulfonyl groups comprising a halogenated hydrocarbyl may be trifluoromethylsulfonyl, pentafluoroethylsulfonyl, pentafluorophenylsulfonyl, heptafluoropropylsufonyl, nonafluorobutylsulfonyl, and like.

In one embodiment, the radialene and/or the quinodimethane compound may be comprised in a hole injection, hole transporting and/or a hole generation layer.

In one embodiment, the radialene compound may have Formula (XX) and/or the quinodimethane compound may have Formula (XXIa) or (XXIb):

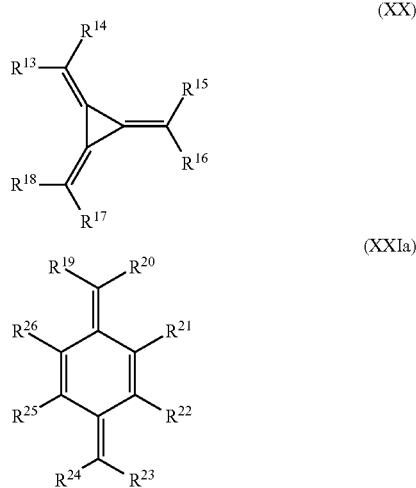

(XX)

(XXIa)

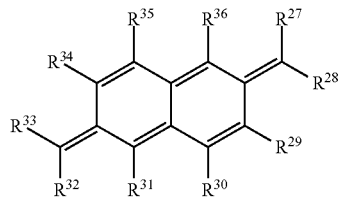

(XXIb)

wherein $R^{13}$, $R^{14}$, $R^{15}$, $R^{16}$, $R^{17}$, $R^{18}$, $R^{19}$, $R^{20}$, $R^{23}$, $R^{24}$, $R^{27}$, $R^{28}$, $R^{32}$, $R^{33}$ are independently selected from above mentioned electron withdrawing groups and $R^{21}$, $R^{22}$, $R^{25}$, $R^{26}$, $R^{29}$, $R^{30}$, $R^{31}$, $R^{34}$, $R^{35}$ and $R^{36}$ are independently selected from H, halogen and above mentioned electron withdrawing groups.

Hereinafter, the embodiments are illustrated in more detail with reference to examples. However, the present disclosure is not limited to the following examples. Reference will now be made in detail to the exemplary aspects.

DETAILS AND DEFINITIONS OF THE INVENTION

In the present specification, when a definition is not otherwise provided, an "alkyl group" may refer to an aliphatic hydrocarbon group. The alkyl group may refer to "a saturated alkyl group" without any double bond or triple bond. The term "alkyl" as used herein shall encompass linear as well as branched and cyclic alkyl. For example, $C_3$-alkyl may be selected from n-propyl and iso-propyl. Likewise, $C_4$-alkyl encompasses n-butyl, sec-butyl and t-butyl. Likewise, $C_6$-alkyl encompasses n-hexyl and cyclohexyl.

The subscribed number n in $C_n$ relates to the total number of carbon atoms in the respective alkyl, arylene, heteroarylene or aryl group.

The term "aryl" or "arylene" as used herein shall encompass aromatic groups like phenyl ($C_6$-aryl), fused aromatics, such as naphthalene, anthracene, phenanthracene, tetracene etc. Further encompassed are biphenyl and oligo- or polyphenyls, such as terphenyl etc. Further encompassed by the term "aryl", respectively "arylene", may be such groups in which two or more different aromatic groups are connected with each other via (at least) one $sp^3$-hybridized carbon atoms. In other words, G may be provided that the group G comprises at least one $sp^3$-hybridized carbon atom when it is selected as an aryl group or a heteroaryl group. In this case, it may be provided that the group G is linked to the benzoacridine moiety by a direct bond to the $Sp^3$-hybridized carbon atom. Exemplary aryl (respectively arylene) groups containing $sp^3$-hybridized carbon atom(s) are groups, such as substituted or unsubstituted fluorenyl (for example 9,9-diphenyl-9H-fluorenyl or 9,9-spirobi[9H-fluorene]yl, 9,9-dimethyl-9H-fluorenyl etc.), wherein, of course, other derivatives comprising other alkyl groups, other aryl groups etc. are included. "Arylene" respectively "heteroarylene", refers to groups to which two further moieties are attached. In the present specification the term "aryl group" or "arylene group" may refer to a group comprising at least one hydrocarbon aromatic moiety, and all the elements of the hydrocarbon aromatic moiety may have p-orbitals which form conjugation, for example a phenyl group, a naphtyl group, an anthracenyl group, a phenanthrenyl group, a pyrenyl group, a fluorenyl group and the like. The aryl or arylene group may include a monocyclic or fused ring polycyclic (i.e., rings sharing adjacent pairs of carbon atoms) functional group.

The term "condensed aryl(ene) group" refers to an aryl group comprising at least two aromatic rings which are fused to each other by sharing two carbon atoms with each other. In this regard, it may be provided that the condensed aryl group (or the condensed arylene group) comprises more than two fused rings wherein each of the rings is fused with at least one other aryl ring of the condensed aryl(ene) by sharing with this one (or more) further ring(s) two carbon atoms. Non-limiting examples of such condensed aryl groups are fluoranthenyl, chrysenyl, pyrenyl etc.

The term "alkenyl" as used herein refers to a group —$CR^1$=$CR^2R^3$ comprising a carbon-carbon double bond.

The term "perhalogenated" as used herein refers to a hydrocarbyl group wherein all of the hydrogen atoms of the hydrocarbyl group are replaced by halogen (F, Cl, Br, I) atoms.

The term "alkoxy" as used herein refers to a structural fragment of the Formula —OR with R being hydrocarbyl, preferably alkyl or cycloalkyl.

The term "heteroaryl" as used herein refers to aromatic or aryl groups in which at least one carbon atom is substituted with a heteroatom, preferably selected from N, O, S, B or Si.

The subscripted number n in $C_n$-heteroaryl merely refers to the number of carbon atoms excluding the number of heteroatoms. In this context, it is clear that a $C_3$ heteroarylene group is an aromatic compound comprising three carbon atoms, such as pyrazol, imidazole, oxazole, thiazole and the like.

The term "heteroaryl" may refer to aromatic heterocycles (aryl) with at least one heteroatom, and all the elements of the hydrocarbon heteroaromatic moiety may have p-orbitals which form conjugation. The heteroatom may be selected from N, O, S, B, Si, P, Se, preferably from N, O and S. A heteroarylene ring may comprise at least 1 to 3 heteroatoms. Preferably a heteroarylene ring may comprise at least 1 to 3 heteroatoms individually selected from N, S and/or O.

The term "heteroaryl" as used herewith shall encompass pyridine, quinoline, benzoquinoline, quinazoline, benzoquinazoline, pyrimidine, pyrazine, triazine, benzimidazole, benzothiazole, benzo[4,5]thieno[3,2-d]pyrimidine, carbazole, xanthene, phenoxazine, benzoacridine, dibenzoacridine, dibenzofurane, dibenzothiophene, phenanthroline and the like.

The term "fluorinated" as used herein refers to a hydrocarbon group in which at least one of the hydrogen atoms comprised in the hydrocarbon group is substituted by a fluorine atom. Fluorinated groups in which all of the hydrogen atoms thereof are substituted by fluorine atoms are referred to as perfluorinated groups and are particularly addressed by the term "fluorinated".

In terms of the invention, a group is "substituted with" another group if one of the hydrogen atoms comprised in this group is replaced by another group, wherein the other group is the substituent.

In terms of the invention, the expression "between" with respect to one layer being between two other layers does not exclude the presence of further layers which may be arranged between the one layer and one of the two other layers. In terms of the invention, the expression "in direct contact" with respect to two layers being in direct contact with each other means that no further layer is arranged between those two layers. One layer deposited on the top of another layer is deemed to be in direct contact with this layer.

With respect to the inventive organic semiconductive layer as well as with respect to the inventive compound, the compounds mentioned in the experimental part are most preferred.

The inventive organic electronic device may be an organic electroluminescent device (OLED) an organic photovoltaic device (OPV), a lighting device, or an organic field-effect transistor (OFET). A lighting device may be any of the devices used for illumination, irradiation, signaling, or projection. They are correspondingly classified as illuminating, irradiating, signaling, and projecting devices. A lighting device usually consists of a source of optical radiation, a device that transmits the radiant flux into space in the desired direction, and a housing that joins the parts into a single device and protects the radiation source and light-transmitting system against damage and the effects of the surroundings.

According to another aspect, the organic electroluminescent device according to the present invention may comprise more than one emission layer, preferably two or three emission layers.

An OLED comprising more than one emission layer is also described as a tandem OLED or stacked OLED.

The organic electroluminescent device (OLED) may be a bottom- or top-emission device.

Another aspect is directed to a device comprising at least one organic electroluminescent device (OLED).

A device comprising organic light-emitting diodes is for example a display or a lighting panel.

In the present invention, the following defined terms, these definitions shall be applied, unless a different definition is given in the claims or elsewhere in this specification.

In the context of the present specification the term "different" or "differs" in connection with the matrix material or matrix compound means that the matrix material or matrix compound differs in their structural Formula.

The terms "OLED" and "organic light-emitting diode" are simultaneously used and have the same meaning. The term "organic electroluminescent device" as used herein may comprise both organic light emitting diodes as well as organic light emitting transistors (OLETs).

As used herein, "weight percent", "wt.-%", "percent by weight", "% by weight", and variations thereof refer to a composition, component, substance or agent as the weight of that component, substance or agent of the respective electron transport layer divided by the total weight of the respective electron transport layer thereof and multiplied by 100. It is under-stood that the total weight percent amount of all components, substances and agents of the respective electron transport layer and electron injection layer are selected such that it does not exceed 100 wt.-%.

As used herein, "volume percent", "vol.-%", "percent by volume", "% by volume", and variations thereof refer to a composition, component, substance or agent as the volume of that component, substance or agent of the respective electron transport layer divided by the total volume of the respective electron transport layer thereof and multiplied by 100. It is understood that the total volume percent amount of all components, substances and agents of the cathode layer are selected such that it does not exceed 100 vol.-%.

All numeric values are herein assumed to be modified by the term "about", whether or not explicitly indicated. As used herein, the term "about" refers to variation in the numerical quantity that can occur. Whether or not modified by the term "about" the claims include equivalents to the quantities.

It should be noted that, as used in this specification and the appended claims, the singular forms "a", "an", and "the" include plural referents unless the content clearly dictates otherwise.

The term "free of", "does not contain", "does not comprise" does not exclude impurities. Impurities have no technical effect with respect to the object achieved by the present invention.

In the context of the present specification the term "essentially non-emissive" or "non-emissive" means that the contribution of the compound or layer to the visible emission spectrum from the device is less than 10%, preferably less than 5% relative to the visible emission spectrum. The visible emission spectrum is an emission spectrum with a wavelength of about ≥380 nm to about ≥780 nm.

Preferably, the organic semiconducting layer comprising the compound of Formula (I) is essentially non-emissive or non-emitting.

The operating voltage, also named U, is measured in Volt (V) at 10 milliAmpere per square centimeter (mA/cm2).

The candela per Ampere efficiency, also named cd/A efficiency is measured in candela per ampere at 10 milli-Ampere per square centimeter (mA/cm2).

The external quantum efficiency, also named EQE, is measured in percent (%).

The color space is described by coordinates CIE-x and CIE-y (International Commission on Illumination 1931). For blue emission the CIE-y is of particular importance. A smaller CIE-y denotes a deeper blue color.

The highest occupied molecular orbital, also named HOMO, and lowest unoccupied molecular orbital, also named LUMO, are measured in electron volt (eV).

The term "OLED", "organic light emitting diode", "organic light emitting device", "organic optoelectronic device" and "organic light-emitting diode" are simultaneously used and have the same meaning.

The term "life-span" and "lifetime" are simultaneously used and have the same meaning.

The anode electrode and cathode electrode may be described as anode electrode/cathode electrode or anode electrode/cathode electrode or anode electrode layer/cathode electrode layer.

Room temperature, also named ambient temperature, is 23° C.

BRIEF DESCRIPTION OF THE DRAWINGS

These and/or other aspects and advantages of the present invention will become apparent and more readily appreciated from the following description of the exemplary embodiments, taken in conjunction with the accompanying drawings, of which.

DETAILED DESCRIPTION

Figure 1:
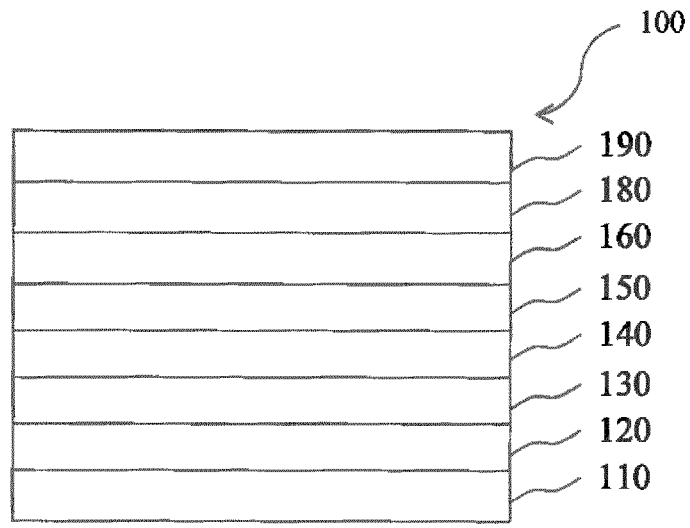
FIG. 1 is a schematic sectional view of an organic light-emitting diode (OLED), according to an exemplary embodiment of the present invention.

Reference will now be made in detail to the exemplary embodiments of the present invention, examples of which are illustrated in the accompanying drawings, wherein like reference numerals refer to the like elements throughout. The exemplary embodiments are described below, in order to explain the aspects of the present invention, by referring to the figures.

Herein, when a first element is referred to as being formed or disposed "on" or "onto" a second element, the first element can be disposed directly on the second element, or one or more other elements may be disposed there between. When a first element is referred to as being formed or disposed "directly on" or "directly onto" a second element, no other elements are disposed there between.

FIG. 1 is a schematic sectional view of an organic light-emitting diode (OLED) 100, according to an exemplary embodiment of the present invention. The OLED 100 includes a substrate 110, an anode 120, a hole injection layer (HIL) 130, a hole transport layer (HTL) 140, an emission layer (EML) 150, an electron transport layer (ETL) 160. The electron transport layer (ETL) 160 is formed on the EML 150. Onto the electron transport layer (ETL) 160, an electron injection layer (EIL) 180 is disposed. The cathode 190 is disposed directly onto the electron injection layer (EIL) 180.

Instead of a single electron transport layer 160, optionally an election transport layer stack (ETL) can be used.

Figure 2:
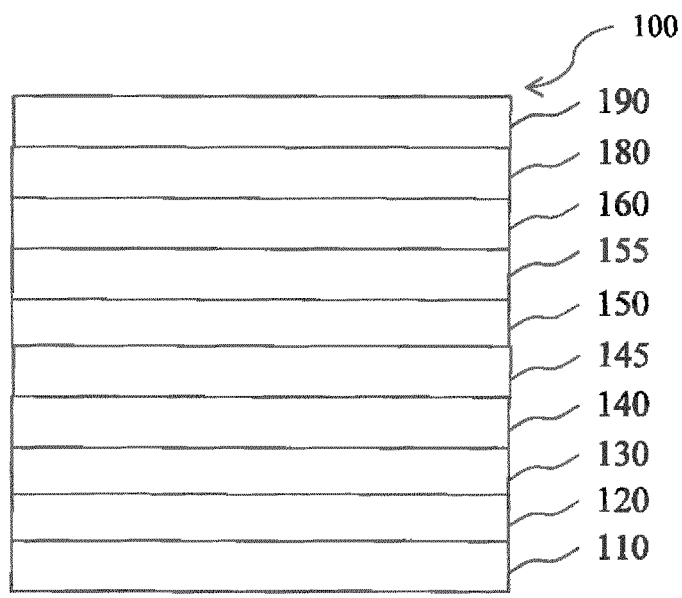
FIG. 2 is a schematic sectional view of an OLED, according to an exemplary embodiment of the present invention.

FIG. 2 is a schematic sectional view of an OLED 100, according to another exemplary embodiment of the present invention. FIG. 2 differs from FIG. 1 in that the OLED 100 of FIG. 2 comprises an electron blocking layer (EBL) 145 and a hole blocking layer (HBL) 155.

Referring to FIG. 2, the OLED 100 includes a substrate 110, an anode 120, a hole injection layer (HIL) 130, a hole transport layer (HTL) 140, an electron blocking layer (EBL) 145, an emission layer (EML) 150, a hole blocking layer (HBL) 155, an electron transport layer (ETL) 160, an electron injection layer (EIL) 180 and a cathode electrode 190.

Preferably, the organic semiconducting layer comprising a compound of Formula (I) may be an HBL.

Figure 3:
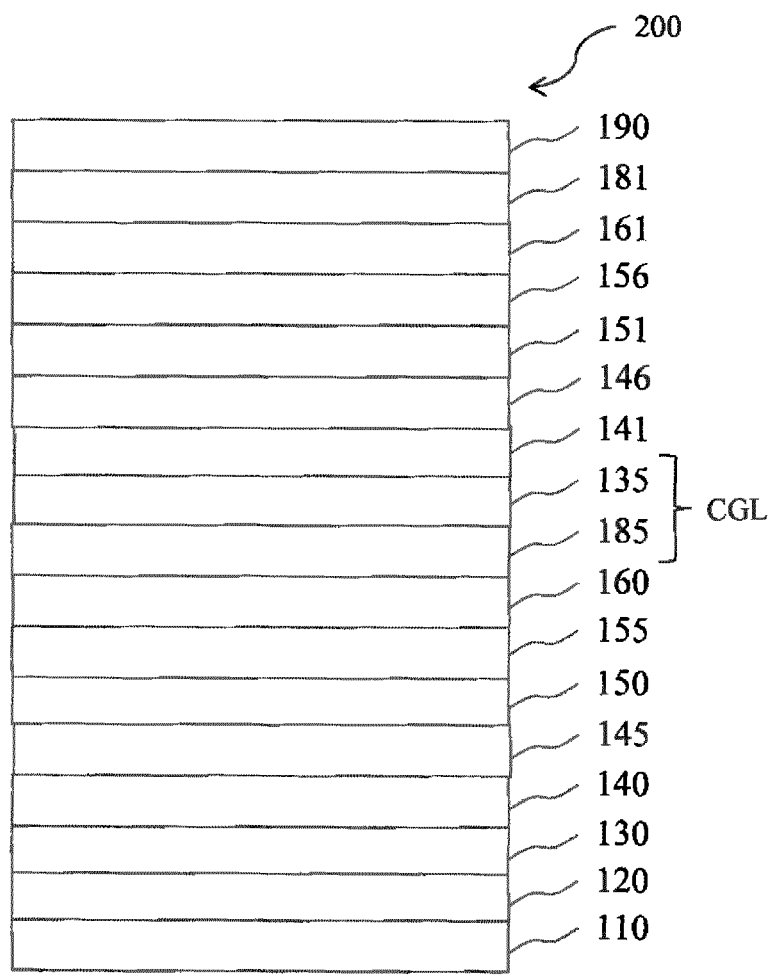
FIG. 3 is a schematic sectional view of a tandem OLED comprising a charge generation layer, according to an exemplary embodiment of the present invention.

FIG. 3 is a schematic sectional view of a tandem OLED 200, according to another exemplary embodiment of the present invention. FIG. 3 differs from FIG. 2 in that the OLED 100 of FIG. 3 further comprises a charge generation layer (CGL) and a second emission layer (151).

Referring to FIG. 3, the OLED 200 includes a substrate 110, an anode 120, a first hole injection layer (HIL) 130, a first hole transport layer (HTL) 140, a first electron blocking layer (EBL) 145, a first emission layer (EML) 150, a first hole blocking layer (HBL) 155, a first electron transport layer (ETL) 160, an n-type charge generation layer (n-type CGL) 185, a hole generating layer (p-type charge generation layer; p-type GCL) 135, a second hole transport layer (HTL) 141, a second electron blocking layer (EBL) 146, a second emission layer (EML) 151, a second hole blocking layer (EBL) 156, a second electron transport layer (ETL) 161, a second electron injection layer (EIL) 181 and a cathode 190.

Preferably, the organic semiconducting layer comprising a compound of Formula (I) may be the first ETL, n-type CGL and/or second ETL.

While not shown in FIG. 1, FIG. 2 and FIG. 3, a sealing layer may further be formed on the cathode electrodes 190, in order to seal the OLEDs 100 and 200. In addition, various other modifications may be applied thereto.

Hereinafter, one or more exemplary embodiments of the present invention will be described in detail with, reference to the following examples. However, these examples are not intended to limit the purpose and scope of the one or more exemplary embodiments of the present invention.

Experimental Data

Melting Point

The melting point (mp) is determined as peak temperatures from the DSC curves of the above TGA-DSC measurement or from separate DSC measurements (Mettler Toledo DSC822e, heating of samples from room temperature to completeness of melting with heating rate 10 K/min under a stream of pure nitrogen. Sample amounts of 4 to 6 mg are placed in a 40 μL Mettler Toledo aluminum pan with lid, a <1 mm hole is pierced into the lid).

Glass Transition Temperature

The glass transition temperature (Tg) is measured under nitrogen and using a heating rate of 10 K per min in a Mettler Toledo DSC 822e differential scanning calorimeter as described in DIN EN ISO 11357, published in March 2010.

Rate Onset Temperature

The rate onset temperature ($T_{RO}$) is determined by loading 100 mg compound into a VTE source. As VTE source a point source for organic materials may be used as supplied by Kurt J. Lesker Company (www.lesker.com) or CreaPhys GmbH (http://www.creaphys.com). The VTE source is heated at a constant rate of 15 K/min at a pressure of less than $10^{-5}$ mbar and the temperature inside the source measured with a thermocouple. Evaporation of the compound is detected with a QCM detector which detects deposition of the compound on the quartz crystal of the detector. The deposition rate on the quartz crystal is measured in Angstrom per second. To determine the rate onset temperature, the deposition rate is plotted against the VTE source temperature. The rate onset is the temperature at which noticeable deposition on the QCM detector occurs. For accurate results, the VTE source is heated and cooled three time and only results from the second and third run are used to determine the rate onset temperature.

To achieve good control over the evaporation rate of an organic compound, the rate onset temperature may be in the range of 200 to 255° C. If the rate onset temperature is below 200° C. the evaporation may be too rapid and therefore difficult to control. If the rate onset temperature is above 255° C. the evaporation rate may be too low which may result in low tact time and decomposition of the organic compound in VTE source may occur due to prolonged exposure to elevated temperatures.

The rate onset temperature is an indirect measure of the volatility of a compound. The higher the rate onset temperature the lower is the volatility of a compound.

Reduction Potential

The reduction potential is determined by cyclic voltammetry with potenioststic device Metrohm PGSTAT30 and software Metrohm Autolab GPES at room temperature. The redox potentials given at particular compounds were measured in an argon de-aerated, dry 0.1M THF solution of the tested substance, under argon atmosphere, with 0.1M tetrabutylammonium hexafluorophosphate supporting electrolyte, between platinum working electrodes and with an Ag/AgCl pseudo-standard electrode (Metrohm Silver rod electrode), consisting of a silver wire covered by silver chloride and immersed directly in the measured solution, with the scan rate 100 mV/s. The first run was done in the broadest range of the potential set on the working electrodes, and the range was then adjusted within subsequent runs appropriately. The final three runs were done with the addition of ferrocene (in 0.1M concentration) as the standard. The average of potentials corresponding to cathodic and anodic peak of the studied compound, after subtraction of the average of cathodic and anodic potentials observed for the standard $Fc^+/Fc$ redox couple, afforded finally the values reported above. All studied compounds as well as the reported comparative compounds showed well-defined reversible electrochemical behaviour.

Dipole Moment

The dipole moment $|\vec{\mu}|$ of a molecule containing N atoms is given by:

$$\vec{\mu} = \sum_{i}^{N} q_i \vec{r}_i$$

$$|\vec{\mu}| = \sqrt{\mu_x^2 + \mu_y^2 + \mu_z^2}$$

where $q_i$ and $\vec{r}_i$ are the partial charge and position of atom i in the molecule.

The dipole moment is determined by a semi-empirical molecular orbital method.

The geometries of the molecular structures are optimized using the hybrid functional B3LYP with the 6-31G* basis set in the gas phase as implemented in the program package TURBOMOLE V6.5 (TURBOMOLE GmbH, Litzenhardtstrasse 19, 76135 Karlsruhe, Germany). If more than one conformation is viable, the conformation with the lowest total energy is selected to determine the bond lengths of the molecules.

Calculated HOMO and LUMO

The HOMO and LUMO are calculated with the program package TURBOMOLE V6.5 (TURBOMOLE GmbH, Litzenhardtstrasse 19, 76135 Karlsruhe, Germany). The optimized geometries and the HOMO and LUMO energy levels of the molecular structures are determined by applying the hybrid functional B3LYP with a 6-31G* basis set in the gas phase. If more than one conformation is viable, the conformation with the lowest total energy is selected.

Synthesis Procedures

Molecules Synthesized

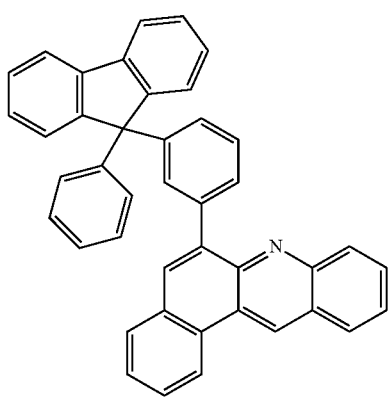

A-1

A-2
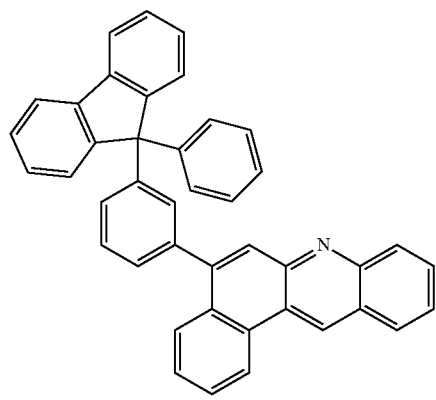
A-3
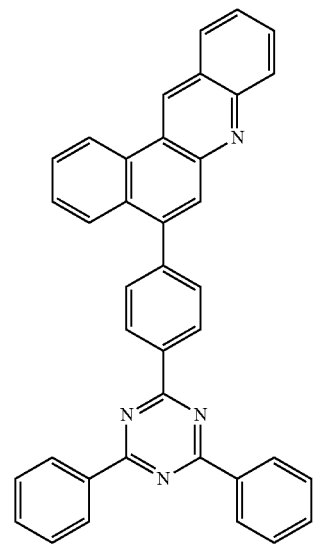
A-4
A-5
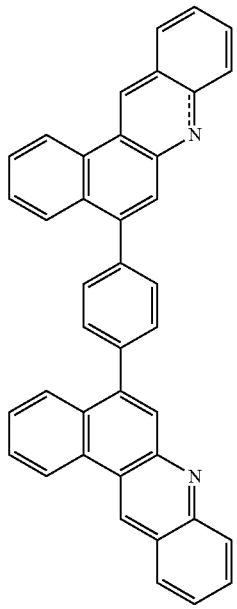
16573-42-5
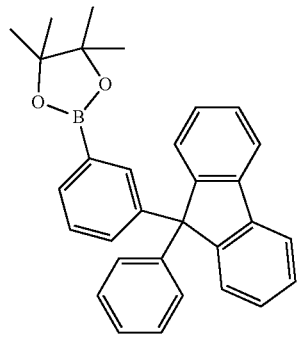
1260032-45-8

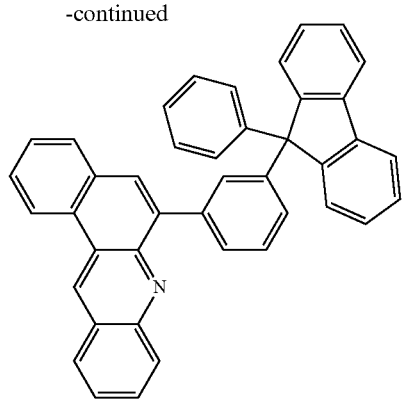

6-chlorobenzo[a]acridine

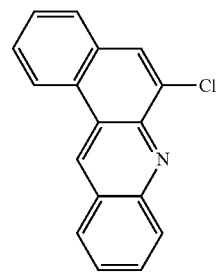 [SMILES: Clc1cc2ccccc2c2cc3ccccc3nc12]

5,6-dihydrobenzo[a]acridine (10.4 g, 45.0 mmol) and 1-chloropyrrolidine-2,5-dione (11.6 g, 90.0 mmol) were placed in a flask under nitrogen atmosphere and dissolved in acetonitrile (230 mL) at room temperature. The solution was heated to 80° C. and stirred for 5 h. After cooling down to room temperature, the resulting precipitate was isolated by suction filtration and washed with acetonitrile. The solid was dissolved in chloroform (250 mL) and washed first with Na$_2$CO$_3$ $_{(aq.)}$ (50 mL) and then with water. Organic phase was dried over Na$_2$SO$_4$, drying agent was filtered off and solvents were completely removed under pressure. Product was recrystallized in cyclohexane and dried under vacuum to afford 4.7 g (40%) of a solid. GC-MS>99%.

6-(3-(9-phenyl-9H-fluoren-9-yl)phenyl)benzo[a]acridine (Compound A-1)

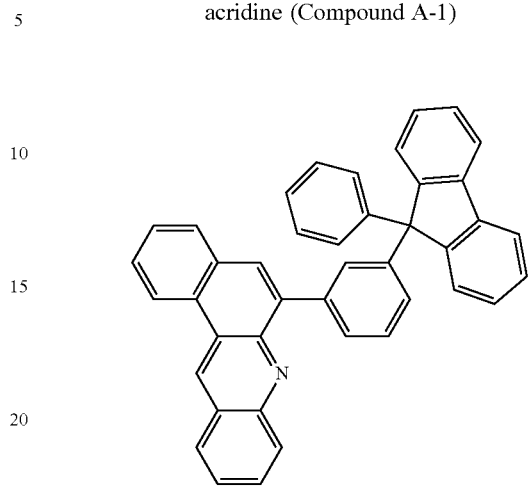

A flask was flushed with nitrogen and charged with 6-chlorobenzo[a]acridine (2.1 g, 8.0 mmol), 4,4,5,5-tetramethyl-2-(3-(9-phenyl-9H-fluoren-9-yl)phenyl)-1,3,2-dioxaborolane (4.3 g, 9.6 mmol), chloro(crotyl)(2-dicydohexylphosphino-2',6'-dimethoxybiphenyl)palladium(II) (97 mg, 0.16 mmol), potassium phosphate (3.4 g, 16.0 mmol). A mixture of deaerated tetrahydrofurane/water (4:1, 80 mL) was added and the reaction mixture was heated to 50° C. under a nitrogen atmosphere overnight. After cooling down to room temperature, the resulting precipitate was isolated by suction filtration and washed with water. The crude product was then dissolved in hot chloroform (300 mL) and filtered through a silicagel pad. After rinsing with additional hot chloroform (600 mL) and hot chlorobenzene (600 mL), the filtrate was concentrated under reduced pressure to a minimal volume and n-hexane (200 mL) was added. The resulting suspension was stirred at room temperature and the precipitate was collected by suction filtration. The compound was finally recrystallized in acetonitrile/tetrahydrofurane (40/60 mL) to yield 3.0 g (70%) of a solid after drying. Final purification was achieved by sublimation. m/z=546 ([M+H]$^+$), 568 ([M+Na]$^+$).

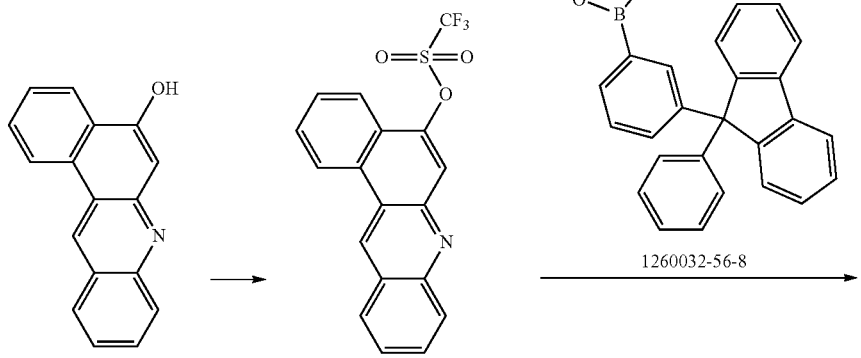

50637-33-7

1260032-56-8

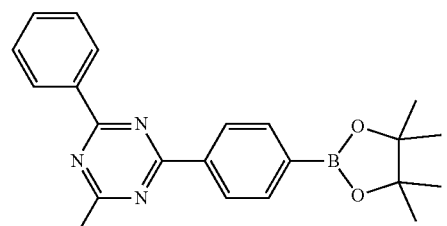
-continued
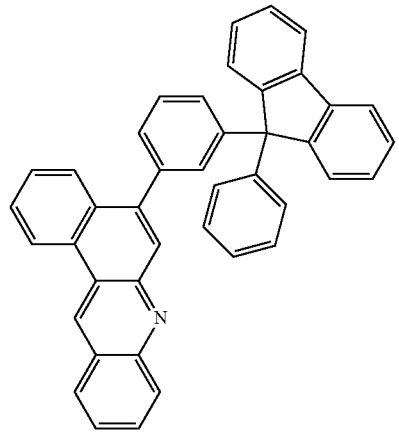
1219956-23-6
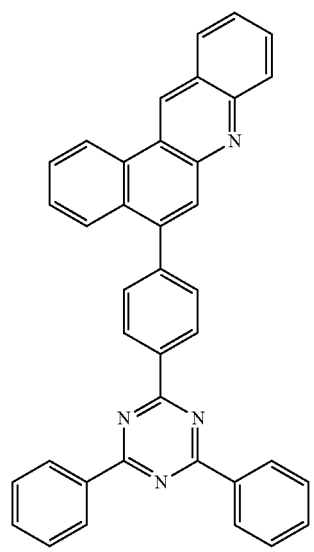
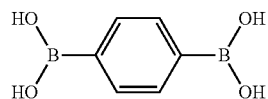
4612-26-4

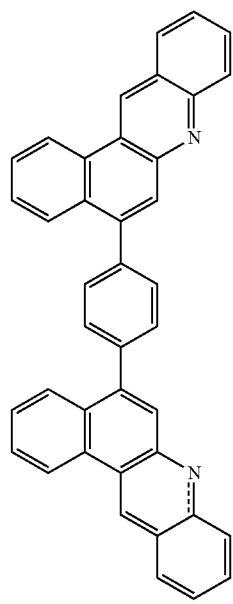 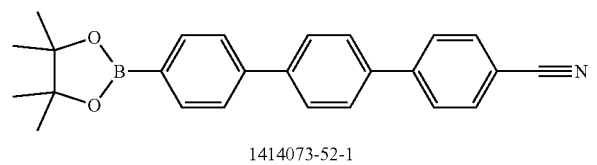 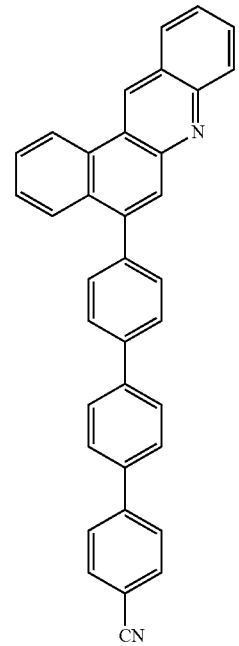

Benzo[a]acridin-5-yl trifluoromethanesulfonate 5-(3-(9-Phenyl-9H-fluoren-9-yl)phenyl)benzo[a]acridine (Compound A-2)

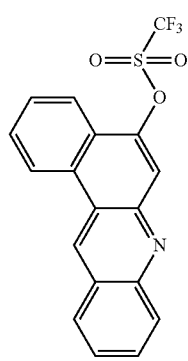 [SMILES: O=S(=O)(Oc1cc2nc3ccccc3cc2c2ccccc12)C(F)(F)F]

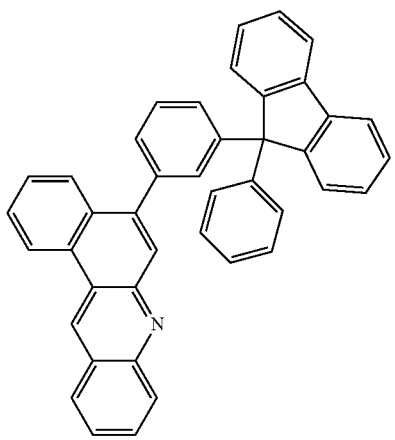 [SMILES: c1ccc(C2(c3cccc(-c4cc5nc6ccccc6cc5c5ccccc45)c3)c3ccccc3-c3ccccc32)cc1]

Benzo[a]acridin-5-ol (6.5 g, 26.5 mmol) was suspended in anhydrous dichloromethane (240 mL) in a flask equipped with a drying tube filled with calcium chloride. Pyridine (4.2 mL, 53.0 mmol) was added and the mixture was cooled down to 0° C. Trifluoromethanesulfonic anhydride (5.3 mL, 31.8 mmol) was added dropwise and the solution was stirred overnight. Solution was again cooled down to 0° C. Pyridine (1.0 mL, 13.3 mmol) and trifluoromethanesulfonic anhydride (1.3 mL, 8.0 mmol) were added and the solution was stirred overnight. Crude reaction was washed with water, dried over Na$_2$SO$_4$, and purified by column chromatography using dichloromethane as eluent. Organic solvents from the column were partially removed under reduced pressure and n-hexane was added to induce precipitation. The precipitate was collected by suction filtration to yield 4.0 g (40%) of a solid after drying.

A flask was flushed with nitrogen and charged with benzo[a]acridin-5-yl trifluoromethanesulfonate (3.9 g, 10.3 mmol), 4,4,5,5-tetramethyl-2-(3-(9-phenyl-9H-fluoren-9-yl)phenyl)-1,3,2-dioxaborolane (5.1 g, 11.4 mmol), tetrakis(triphenylphosphin)palladium(0) (239 mg, 0.21 mmol), potassium carbonate (2.9 g, 20.7 mmol). A mixture of deaerated tetrahydrofurane/water (4:1, 50 mL) was added and the reaction mixture was heated to reflux under a nitrogen atmosphere overnight. After cooling down to room temperature, the solvents were partially removed under reduced pressure and dichloromethane first and then hexane were added. The resulting precipitate was isolated by suction filtration and washed with water. The crude product was then dissolved in hot chlorobenzene (200 mL) and filtered through a silicagel pad. After rinsing with additional hot chlorobenzene (450 mL) and tetrahydrofurane (50 mL), the solvents were completely removed under reduced pressure. The crude product was dissolved in hot tetrahydrofurane and acetonitrile (50 mL) was added to induce the precipitation. The precipitate was collected by suction filtration. The recrystallization step was repeated one more time to yield 4.4 g (79%) of a solid after drying. Final purification was achieved by sublimation. m/z=546 ([M+H]$^+$).

5-(4-(4,6-Diphenyl-1,3,5-triazin-2-yl)phenyl)benzo[a]acridine (Compound A-3)

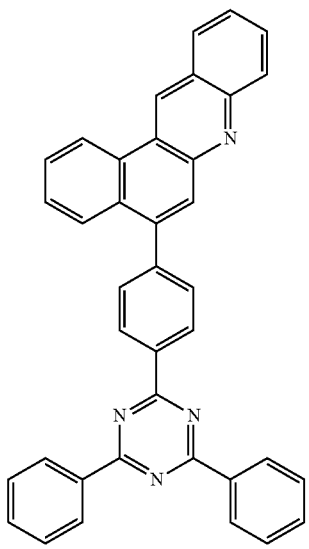 [SMILES: c1ccc(-c2nc(-c3ccccc3)nc(-c3ccc(-c4cc5nc6ccccc6cc5c5ccccc45)cc3)n2)cc1]

A flask was flushed with nitrogen and charged with benzo[a]acridin-5-yl trifluoromethanesulfonate (10.0 g, 26.5 mmol), 2,4-diphenyl-6-(4-(4,4,5,5-tetramethyl-1,3,2-dioxaborolan-2-yl)phenyl)-1,3,5-triazine (12.7 g, 29.2 mmol), tetrakis(triphenylphosphin)palladium(0) (612 mg, 0.53 mmol), and potassium carbonate (7.32 g, 53 mmol). A mixture of deaerated tetrahydrofurane/water (5:1, 150 mL) was added and the reaction mixture was heated to 75° C. under a nitrogen atmosphere overnight. After cooling down to 5° C., the resulting precipitate was isolated by suction filtration and washed with tetrahydrofurane (3×10 mL), n-hexane (3×20 mL), water (1.3 L) and methanol (2×30 mL). The crude product was further purified by column chromatography (silicagel, chlorobenzene to chlorobenzene/ethanol 96/4). The filtrate was concentrated under reduced pressure to a volume of 200 mL and stirred at room temperature over 2 hours. The resulting precipitate was collected by suction filtration and washed with chlorobenzene to yield 10.8 g (76%) of a bright yellow solid after drying. Final purification was achieved by sublimation. m/z=537.1 ([M+H]$^+$).

1,4-Bis(benzo[a]acridin-5-yl)benzene (Compound A-5)

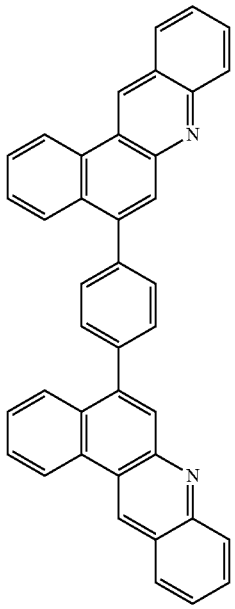 [SMILES: c1ccc2nc3cc(-c4ccc(-c5cc6nc7ccccc7cc6c6ccccc56)cc4)c4ccccc4c3cc2c1]

A solution of benzo[a]acridin-5-yl trifluoromethanesulfonate (12 g, 31.8 mmol), 1,4-phenylenediboronic acid (2.64 g, 15.9 mmol) and potassium carbonate (8.79 g, 63.6 mmol) in THF/water (5:1, 225 mL) was degassed with nitrogen over 45 minutes. Tetrakis(triphenylphosphin)palladium(0) (730 mg, 0.64 mmol) was added and the reaction mixture was heated to 75° C. under nitrogen atmosphere overnight. After cooling down, the resulting precipitate was isolated by suction filtration and washed with water and methanol. The crude product was further purified by soxhlet extraction in chlorobenzene to yield 4.9 g (58%) of a grey greenish solid after drying. Final purification was achieved by sublimation. m/z=533.1 ([M+H]$^+$).

4-(benzo[a]acridin-5-yl-[1,1':4',1''-terphenyl]-4-carbonitrile (Compound A-4)

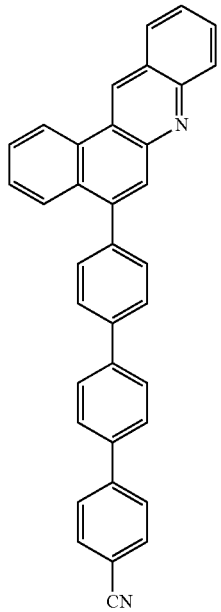 [SMILES: N#Cc1ccc(-c2ccc(-c3ccc(-c4cc5nc6ccccc6cc5c5ccccc45)cc3)cc2)cc1]

A solution of potassium carbonate (5.8 g, 42.0 mmol) in water (30 mL) and a solution of 4"-(4,4,5,5-tetramethyl-1,3,2-dioxaborolan-2-yl)-[1,1':4',1"-terphenyl]-4-carbonitrile (8.0 g, 21 mmol) and benzo[a]acridin-5-yl trifluoromethanesulfonate (7.92 g, 21 mmol) in tetrahydrofuran (120 mL) were degassed with nitrogen over 30 minutes. After the two solutions were combined, tetrakis(triphenylphosphin)palladium(0) (485 mg, 0.42 mmol) was added and the reaction mixture was heated to 70° C. under a nitrogen atmosphere overnight. After cooling down to 5° C., the resulting precipitate was isolated by suction filtration and washed with tetrahydrofuran, water and methanol. The crude product was then dissolved in chloroform and filtered through a pad of silica gel. After rinsing with additional hot chloroform (1 L) and (chloroform/ethyl acetate—10/1) (600 mL), the filtrate was concentrated under reduced pressure to a volume of 50 mL and n-hexane was added. The resulting precipitate was collected by suction filtration and washed with n-hexane. The crude product was further purified by recrystallization from chlorobenzene to yield 8.3 g (82%) of a bright yellow solid after drying. Final purification was achieved by sublimation. m/z=483.1 ([M+H]$^+$).

General Procedure for Fabrication of OLEDs

For the top emission OLED devices of example-1 and of the comparative example a substrate with dimensions of 150 mm×150 mm×0.7 mm was ultrasonically cleaned with a 2% aquatic solution of Deconex FPD 211 for 7 minutes and then with pure water for 5 minutes, and dried for 15 minutes in a spin rinse dryer. Subsequently, Ag was deposited as anode at a pressure of 10-5 to 10-7 mbar.

Then, HT-1 and D-1 were vacuum co-deposited on the anode to form a HIL. Then, HT-1 was vacuum deposited on the HIL, to form an HTL. Then, HT-2 was vacuum deposited on the HTL to form an electron blocking layer (EBL).

Afterwards the emission layer was formed on the EBL by co-deposition of HOST-1 and EMITTER-1.

Then, the ET-1 was vacuum deposited onto the emission layer to form the hole blocking layer (HBL). Then, the electron transport layer was formed on the hole blocking layer by co-depositing a compound of formula (I) and LiQ for example-1. For the comparative example the electron transport layer was formed on the hole blocking layer by co-depositing the compound comparative-1 and LiQ.

Then, the electron injection layer is formed on the electron transporting layer by depositing Yb.

Ag:Mg is then evaporated at a rate of 0.01 to 1 Å/s at 10-7 mbar to form a cathode.

A cap layer of HT-1 is formed on the cathode.

The details of the layer stack in the top emission OLED devices are given below. A slash "/" separates individual layers. Layer thicknesses are given in squared brackets [ . . . ], mixing ratios in wt % given in round brackets ( . . . ):

Layer Stack Details:

Ag [100 nm]/HT-1:D-1 (92:8) [10 nm]/HT-1 [118 nm]/HT-2 [5 nm]/H09:BD200 (97:3) [20 nm]/ET-1 [5 nm]/Compound of formula (I): LiQ (1:1) [31 nm]/Yb [2 nm]/Ag:Mg (90:10) [13 nm]/HT-1 [70 nm]

Technical Effect of the Invention

The OLED devices according to the invention show improved efficiency and lifetime at comparable voltage when using the compounds of formula (I) in an electron transport layer instead of the comparative compound.

List of Compounds Used

|  | IUPAC name | Reference |
| --- | --- | --- |
| HT-1 | N-([1,1'-biphenyl]-4yl)-9,9-dimethyl-N-(4-(9-phenyl-9H-carbazol-3-yl)pheny1)-9H-fluoren-2-amine [CAS 1242056-42-3] | US2016322581 |
| HT-2 | N,N-bis(4-(dibenzo[b,d]furan-4-yl)pheny1)-[1,1':4',1"-terphenyl]-4-amine [CAS 1198399-61-9] | JP2014096418 |
| D-1 | 4,4',4"-((1E,1'E,1"E)-cyclopropane-1,2,3-triylidenetris(cyanomethanylylidene))tris(2,3,5,6-tetrafluorobenzonitrile) [CAS 1224447-88-4] | US2008265216 |
| HOST-1 | Ho9 (Fluorecent-blue host material) | Commerically available from Sun Fine Chemicals, Inc., S. Korea |
| EMITTER-1 | BD2000 (Fluorecent-blue emitter material) | Commerically available from Sun Fine Chemicals, Inc., S. Korea |
| ET-1 | 2,4-diphenyl-6-(4',5',6'-triphenyl-[1,1':2',1":3',1'":3'",1''''-quinquephenyl]-3''''-yl)-1,3,5-triazine [CAS 2032364-64-8] | WO2016171358 |
| Comparative-1 | 7(4-(4-([1,1'-biphenyl]-3-yl)-6-phenyl-1,3,5-triazin-2-yl)phenyl)dibenzo[c,h]acridine | – |
| LiQ | 8-Hydroxyquinolinolato-lithium [CAS 850918-68-2] | WO2013079217 |

TABLE 1

Properties of compounds A-1 to A-5 of formula (I) and of comparative compound Comparative-1.

| | | mp [° C.] | Tg [° C.] | $T_{RO}$ [° C.] |
|---|---|---|---|---|
| Comparative-1 | | 317 | 148 | 286 |
| A-1 | | 290 | 128 | 219 |
| A-2 | | 261 | 126 | 202 |

TABLE 1-continued

Properties of compounds A-1 to A-5 of formula (I) and of comparative compound Comparative-1.

|   | mp [° C.] | Tg [° C.] | $T_{RO}$ [° C.] |
|---|---|---|---|
| A-3 | 319 | 124 | 248 |
| A-4 | 288 | 104 | 237 |
| A-5 | 468 | — | 315 |

TABLE 2

Dipole moment, HOMO and LUMO levels of comparative-1 and compounds A1 to A5, simulated by DFT (B3LYP_Gaussian/6-31G*, gas phase)

|   | Dipole Moment [Debye] | HOMO [eV] | LUMO [eV] |
|---|---|---|---|
| Comparative-1 | 1.77 | −5.66 | −2.00 |
| A-1 | 1.86 | −5.54 | −1.85 |
| A-2 | 1.67 | −5.62 | −1.87 |
| A-3 | 1,88 | −5.71 | −2.06 |
| A-4 | 6.69 | −5.73 | −2.02 |
| A-5 | 1.79 | −5.62 | −1.96 |

TABLE 3

Performance of organic electrolumineseent device comprising the compounds of formula (1) as a matrix compound in the electron transport layer. CIE 1931 y = 0.045

| OLED device examples | Matrix compound | n-additive | Operating voltage at 10 mA/cm² (V) | CEff at 10 mA/cm² (cd/A) | LT97 at 30 mA/cm² (hours) |
|---|---|---|---|---|---|
| Comparative example | Comparative-1 | LiQ | 3.58 | 7.18 | 68 |
| Example-1 | A-1 | LiQ | 3.54 | 7.33 | 83 |

The features disclosed in the foregoing description and in the dependent claims may, both separately and in any combination thereof, be material for realizing the aspects of the disclosure made in the independent claims, in diverse forms thereof.

The invention claimed is:

1. Compound of Formula (I)

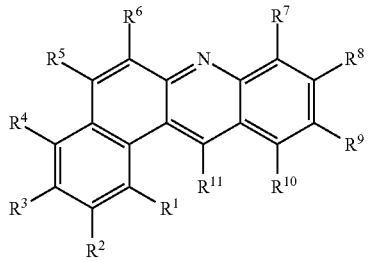

(I)

wherein $R^5$ and/or $R^6$ are independently a group G, wherein G is selected from the group consisting of substituted or unsubstituted $C_6$ to $C_{48}$ aryl, substituted or unsubstituted $C_2$ to $C_{42}$ heteroaryl, and substituted or unsubstituted alkenyl, CN, F, deuterium, nitrile, amino, $P(=Y)(R^{12})_2$ with Y being O or S, wherein $R^{12}$ are independently selected from the group consisting of $C_1$ to $C_{16}$ alkyl, $C_1$ to $C_{16}$ alkoxy, $C_6$ to $C_{18}$ aryl and $C_3$ to $C_{25}$ heteroaryl;

the remaining $R^1$ to $R^{11}$ which are not G are H;

the one or two G may be attached to the benzoacridine moiety in Formula (I) via a direct bond or via a spacer unit;

the one or two spacer unit(s), if present, is/are independently selected from the group consisting of substituted or unsubstituted $C_6$ to $C_{18}$ arylene and substituted or unsubstituted $C_2$ to $C_{20}$ heteroarylene;

the one or more substituent(s) of $R^5$ and/or $R^6$ and/or the spacer unit(s), if present, are independently selected from the group consisting of $C_6$ to $C_{18}$ aryl, wherein it may be provided that adjacent $C_6$ to $C_{18}$ aryl substituents are linked with each other via a direct bond, $C_3$ to $C_{20}$ heteroaryl, $C_1$ to $C_{16}$ alkyl, D, F, $C_1$ to $C_{16}$ alkoxy, CN, CN-substituted $C_6$ to $C_{18}$ aryl, and $P(=Y)(R^{12})_2$ with Y being O or S, wherein $R^{12}$ are independently selected from the group consisting of $C_1$ to $C_{16}$ alkyl, $C_1$ to $C_{16}$ alkoxy, $C_6$ to $C_{18}$ aryl and $C_3$ to $C_{25}$ heteroaryl.

2. Compound according to claim 1, wherein the spacer unit is independently a $C_6$ to $C_{12}$ aryl.

3. Compound according to claim 1, wherein G is independently selected from substituted or unsubstituted $C_6$ to $C_{18}$ aryl, substituted or unsubstituted $C_3$ to $C_{21}$ heteroaryl, or substituted alkenyl.

4. Compound according to claim 1, wherein in case that G is heteroaryl, the heteroaryl is a N-containing heteroaryl.

5. Compound according to claim 1, wherein the one or two groups G is/are independently selected from the group consisting of phenyl, naphthyl, anthracenyl, phenanthryl, fluorenyl, spirobi[fluorenyl], fluoranthenyl, pyridinyl, bipyridinyl, pyrimidinyl, diazinyl, triazinyl, quinolinyl, quinazolinyl, benzimidazolyl, benzoacridinyl, dibenzoacridinyl, benzo[h]quinazolinyl, carbazolyl, carbolinyl, 4,5-diazacabazolyl, phenanthrolinyl, dibenzofuranyl, dimethylphosphineoxide, diphenylphosphineoxide, triphenylalkenyl, [1]benzotieno[3,2-d]pyrimidinyl,

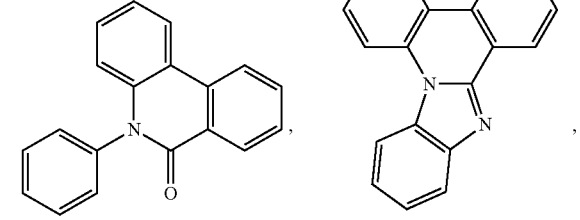

, wherein the respective groups may be substituted or unsubstituted.

6. Compound according to claim 1, wherein the one or more substituent(s), if present on one or more or the groups $R^5$ and/or $R^6$ and/or the spacer unit(s), are independently selected from the group consisting of $C_6$ to $C_{12}$ aryl, $C_5$ to $C_{12}$ heteroaryl, CN-substituted $C_6$ to $C_{12}$ aryl, $C_6$ to $C_{12}$ aryl substituted with $P(=O)(R^{12})_2$ with $R^{12}$ being $C_1$ to $C_{12}$ alkyl or phenyl, $C_1$ to $C_5$ alkyl, CN, $P(=O)(R^{12})_2$ with $R^{12}$ being $C_1$ to $C_5$ alkyl or phenyl.

7. Compound according to claim 1, wherein the number of aromatic rings in the compound of Formula (I) is from 5 to 15.

8. Organic semiconducting layer comprising the compound of Formula (I) according to claim 1.

9. Organic electronic device comprising the organic semiconducting layer according to claim 8.

10. Display device comprising the organic electronic device according to claim 9.

11. Lighting device comprising the organic electronic device according to claim 9.

12. Compound according to claim 6, wherein the one or more substituent(s), if present on one or more or the groups $R^5$ and/or $R^6$ and/or the spacer unit(s), are independently selected from the group consisting of phenyl, naphthyl, biphenyl, CN-substituted phenyl, pyridyl, CN, dibenzofuranyl, dimethylphosphineoxide-substituted phenyl, ethyl, methyl, dimethylphosphine oxide or diphenylphosphine oxide.

13. Compound according to claim 7, wherein the number of aromatic rings in the compound of Formula (I) is from 6 to 10.

* * * * *